United States Patent
Okazaki et al.

(10) Patent No.: US 6,569,643 B2
(45) Date of Patent: May 27, 2003

(54) MAMMALIAN ARTIFICIAL CHROMOSOMES

(76) Inventors: Tsuneko Okazaki, Room 804, Yagoto Family Heights, 24-1,Yamata-dori 3-chome, Showa-ku, Nagoya-shi, Aichi, 466 (JP); Hiroshi Masumoto, c/o Nagoya University, Department of Molecular Biology, School of Science, Furo-cho, Chikusa-ku, Nagoya-shi, Aichi, 464 (JP); Masashi Ikeno, Room 2A, Ashibe Heights, 1-7-2, Motoyama-cho, Chikusa-ku, Nagoya-shi, Aichi, 484-0036 (JP); Howard J. Cooke, c/o Western General Hospital, MRC Human Genetics Unit, Grewe Rd., Edinburgh, EH4 2XU (GB); Brenda Rose Grimes, c/o Western General Hospital, MRC Human Genetics Unit, Grewe Rd., Edinburgh, EH4 2XU (GB)

( * ) Notice: Subject to any disclaimer, the term of this patent is extended or adjusted under 35 U.S.C. 154(b) by 0 days.

(21) Appl. No.: 09/745,600

(22) Filed: Dec. 22, 2000

(65) Prior Publication Data

US 2002/0076811 A1 Jun. 20, 2002

Related U.S. Application Data

(63) Continuation of application No. 09/254,028, filed on Sep. 28, 1999, now Pat. No. 6,297,029.

(30) Foreign Application Priority Data

Aug. 26, 1996 (WO) ................................ PCT/JP96/02381

(51) Int. Cl.[7] ................................ C12P 21/02
(52) U.S. Cl. .................... 435/69.1; 435/320.1
(58) Field of Search ................ 435/6, 320.1, 325, 435/254.2, 254.21, 69.1

(56) References Cited

U.S. PATENT DOCUMENTS

| | | |
|---|---|---|
| 5,270,201 A | 12/1993 | Richards et al. |
| 5,288,625 A | 2/1994 | Hadlaczky |
| 5,695,967 A | 12/1997 | Van Bokkelen |
| 5,712,134 A | 1/1998 | Hadlaczky |
| 5,721,118 A | 2/1998 | Scheffler |
| 5,869,294 A | 2/1999 | Harrington et al. |
| 5,891,691 A | 4/1999 | Hadlaczky |
| 5,981,175 A | 11/1999 | Loring et al. |
| 6,025,155 A | 2/2000 | Hadlaczky et al. |
| 6,133,503 A | 10/2000 | Scheffler |

FOREIGN PATENT DOCUMENTS

| | | |
|---|---|---|
| EP | 0 532 050 A3 | 9/1992 |
| WO | 92/07080 | 4/1992 |
| WO | 93/01292 A | 1/1993 |
| WO | 95/32297 | 11/1995 |
| WO | 96/40965 | 12/1996 |
| WO | 98/08964 | 3/1998 |

OTHER PUBLICATIONS

Adzuma et al., "Primary Structure of the RAD52 Gene in Saccharomyces cerevisiae," *Molecular and Cellular Biology* 4: No. 12 2735–2744 (1984).

Barnett et al., "Telomere directed fragmentation of mammalian chromosomes," *Nucleic Acids Research* 21: No. 1 27–36 (1993).

Barry et al., "Sequence analysis of an 80 kb human neocentromere," *Human Molecular Genetics* 8: No. 2 217–227 (1999).

Brown, et al., "Dissecting the centromere of the human Y chromosome with cloned telomeric DNA," *Human Molecular Genetics* 3:1227–1237 (1994).

Burke, et al., Cloning of Large Segments of Exogenous DNA into Yeast by Means of Artificial Chromosome Vectors; *Science* 236:806–812 (1987).

Campbell, et al., "Generation of a Nested Series of Interstitial Deletions in Yeast Artificial Chromosomes Carrying Human DNA," *Proc. Natl. Acad. Sci. USA* 88:5744–5748 (Jul. 1991).

Choo, "Centromerization," *trends in Cell Biology* 10: 182–188 (May 2000).

Depinet et al., "Characterization of neo–centromeres in marker chromosomes lacking detectable alpha–satellite DNA," *Human Molecular Genetics* 6: No. 8 1195–1204 (1997).

Du Sart et al., "A functional neo–centromere formed through activation of a latent human centromere and consisting of non–alpha–satellite DNA," *Nature Genetics* 16:144–153 (1997).

Farr, et al., "Generation of a human X–derived minichromosome using telomere–associated chromosome fragmentation," *The EMBO Journal* 14: No. 21 5444–5454 (1995).

Goldberg et al., "Surprising Deficiency of CENP–B Binding Sites in African Green Monkey α–satellite DNA: Implications for CENP–B Function at Centromeres," *Molecular and Cellular Biology* 16: No. 9 5156–5167 (1996).

(List continued on next page.)

*Primary Examiner*—James Ketter
(74) *Attorney, Agent, or Firm*—Paul, Hastings, Janofsky & Walker LLP

(57) ABSTRACT

A mammalian chromosome is produced according to the method comprising the steps of introducing a DNA construct comprising a mammalian telomere and a centromere into a mammalian cell, wherein the centromere has a DNA sequence containing a plurality of copies of the CENP-B box sequence consisting of: 5'-NTTCGNNNNANNCGGGN-3', wherein N is any one of A, T, C and G.

11 Claims, 24 Drawing Sheets

(6 of 24 Drawing Sheet(s) Filed in Color)

OTHER PUBLICATIONS

Haaf, et al., "Presence and Abundance of CENP–B Box Sequences in Great Ape Subsets of Primate–Specific Satellite DNA," *Journal of Molecular Evolution* 41:487–491 (1995).

Harrington et al., "Formation of de novo centromeres and construction of first–generation human artificial microchromosomes," *Nature Genetics* 15: 345–355 (1997).

Heller et al., "Mini–chromosomes derived from the human Y chromosome by telomere directed chromosome breakage," *Proc. Natl. Acad. Sci. USA* 93: 7125–7130 (1996).

Hudson et al., "Centromere Protein B Null Mice are Mitotically and Meiotically Normal but Have Lower Body and Testis Weights," *Journal of Cell Biology* 141: 309–319 (1998).

Huxley et al., "Ordering Up Big MACs," *Bio/Technology* 12:586–590 (1994).

Ikeno, et al., "Distribution of CENP–B boxed reflected in Crest centromere antigenic sites on long–range alpha–satellite DNA arrays of human chromosomes 21," *Human Molecular Genetics* vol. 3, No. 8 1245–1257 (1994).

Kipling et al., "CENP–B Binds a Novel Centromeric Sequence in the Asian Mouse *Mus caroli*," *Molecualr and Cellular Biology* 15: No. 8 4009–4020 (1995).

Kitagawa et al., "Analysis of Protein–DNA and Protein–Protein Interactions of Centromere Protein B (CENP–B) and Propterties of the DNA–CENP–B Complex in the Cell Cycle," *Molecular and Cellular Biology* 15: No. 3 1602–1612 (1995).

Larin, et al., "De novo formation of several features of centromere following introduction of a Yalphoid YAC into mammalian cells," *Human Molecular Genetics* vol. 3, No. 5: 689–695 (1994).

Masumoto et al., "A Human Centromere Antigen (CENP–B) Interacts with a Short Specific Sequence in Alphoid DNA, a Human Centromeric Satellite," *Journal of Cell Biology* 109: 1963–1973 (1989).

Masumoto et al., "Alphoid Satellite DNA is Tightly Associated with Centromere Antigens in Human Chromosomes throughout the Cell Cycle," *Experimental Cell Research* 191: 181–196 (1989).

Masumoto et al., "Properties of CENP–B and Its Target Sequence in a Satellite DNA," *NATO ASI Series* H72: 31–43 (1993).

Moroi et al., "Autoantibody to centromere (kinetochore) in scleroderma sera," *Proc. Natl. Acad. sci. USA* 77: No. 3, 1627–1631 (1980).

Muro et al., "Centromere Protein B Assembles Human Centromeric α–satellite DNA at the 17–bp Sequence, CNEP–B Box," *Journal of Cell Biology* 116: No. 3 585–596 (1992).

Neil et al, "Structural instability of human tandemly repeated DNA sequences cloned in yeast artificial chromosome vectors," *Nucleic Acids research* 18: No. 6 1421–1428 (1990).

Okayama et al., "A cDNA Cloning Vector That Permits Expression of cDNA Inserts in Mammalian Cells," *Molecular and Cellular Biology* 3: No. 2 280–289 (1983).

Pachnis et al., "Transfer of a yeast artificial chromosome carrying human DNA from *Saccharomyces cerevisiae* into mammalian cells," *Proc. Natl. Acad. Sci. USA* 87: 5109–5113.

Pavan et al., "Generation of deletion derivatives by targeted transformation of human–derived yeast artificial chromosomes," *Proc. Natl. Acad. Sci. USA* 87: 1300–1304 (1990).

Perez–Castro et al., "Centromeric Protein B Null Mice Are Viable with No Apparent Abnormalities," *Developmental Biology* 201:135–143 (1998).

Saitoh et al., "CENP–C, an Autoantigen in Scleroderma, Is a Component of the Huamn Inner Kinetochore Plate," *Cell* 70:115–125 (1992).

Shen et al., "Human mini–chromosomes in mouse embryonal stem cells," *Human Molecular Genetics* 6: No. 8 1375–1382 (1997).

Shero, et al., "Yeast Artificial Chromosomes Vectors for Efficient Clone Manipulation and Mapping," *Genomics* 10:505–508 (1991).

Sullivan et al., "Identification of centromeric antigens in dicentric Robertsonian translocations: CENP–C and CENP–E are necessary components of functional centromeres," *Human Molecular Genetics* 4: No. 12 2189–2197 (1995).

Taylor et al., "Analysis of extrachromosomal structures containing human centromeric alphoid satellite DNA sequences in mouse cells," *Chromosoma* 105: 70–81 (1996).

Taylor, et al., "Addition of functional human telomeres to YACs," *Human Molecular Genetics* vol. 3, No. 8: 1383–1386 (1994).

Warburton, et al., "Providing a little stability," *Nature* 386:553–555 (1997).

Willard, Chromosome manipulation: A systematic approach toward understanding human chromosome structure and function,: *Proc.Natl.Acad.Sci. USA* 93:6847–6850 (1996).

Yoda et al., "A Human Centromere Protein, CENP–B, Has a DNA Binding Domain Containing Four Potential α Helices at the NH2 Terminus, Which Is Separable from Dimerizing Activity," *Journal of Cell Biology* vol. 119: No. 6 1413–1427 (1992).

Yoda et al., "Centromere Protein B of African Green Monkey Cells: Gene Structure, Cellular Expression, and Centromeric Localization," *Molecular and Cellular Biology* vol. 16: No. 9 5169–5177 (1996).

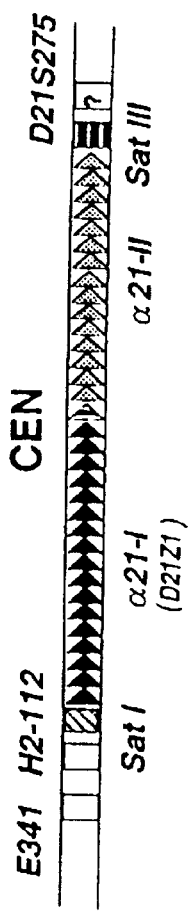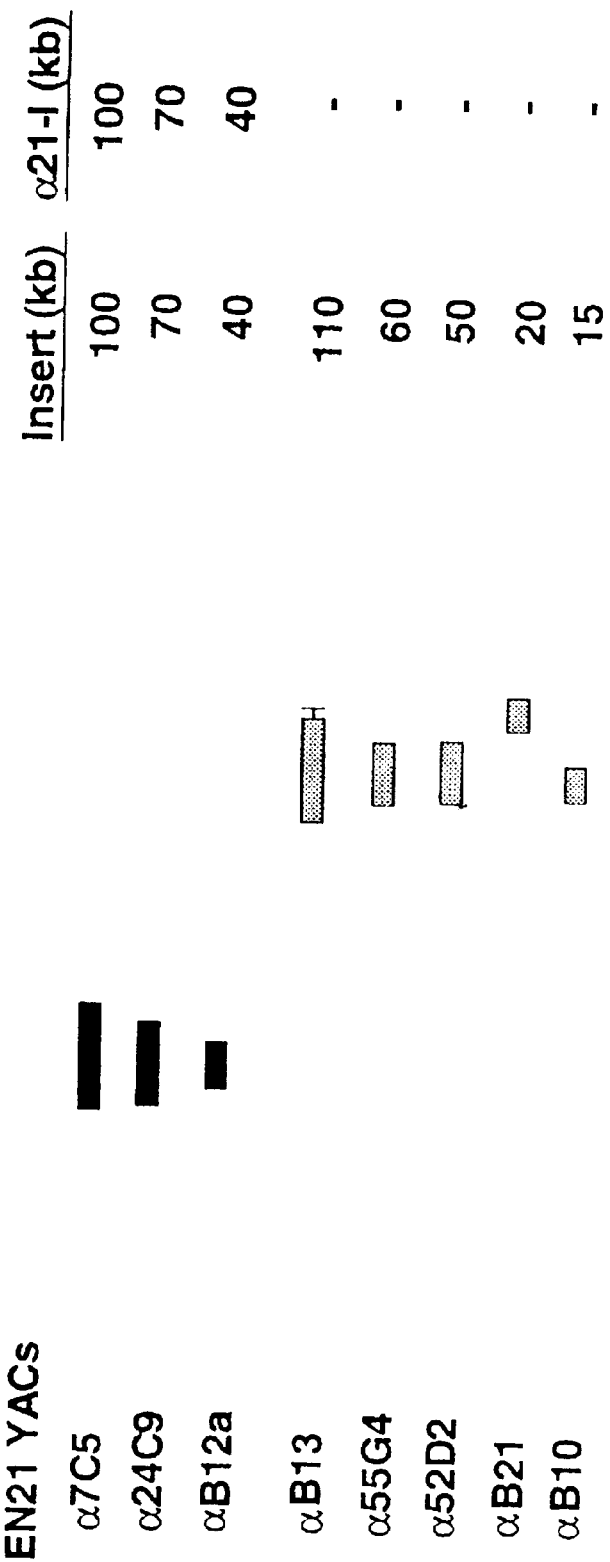
FIG. 3

| YAC clone | α7C5 | αB13 |
|---|---|---|
| Insert[a] | 100 kb | 110 kb |
| Satellite I | - | - |
| α21-I[b] | 103.0 ± 0.3 kb | - |
| α21-II[b] | - | 104.5 ± 0.5 kb |
| Satellite III[b] | - | 1.89 ± 0.01 kb |
| Alu | - | ±[c] |
| CENP-B box[d] | 275 copies | 0 copies |

Efficiency of the minichromosome formation by the alphoid YAC DNA transfections

| Introduced DNA | Introducing method | No. of mitotic cells analyzed by FISH | FISH analysis % of the cells showing the signals | | | | |
|---|---|---|---|---|---|---|---|
| | | | Extrachromosomal | Host chromosomal | | | No signal |
| | | | | Tel | Cen | Arm | |
| α7C5hTEL | Lipofection | 350 (13) | 30.6 (11) | 14.0 (9) | 26.0 (11) | 0.9 (1) | 28.6 (11) |
| | Microinjection | 260# (11) | 27.3 (10) | 17.7 (6) | 27.7 (7) | 3.1 (4) | 29.6 (9) |
| | Total | 610 (24) | 29.2 (21) | 15.6 (15) | 26.7 (18) | 1.8 (5) | 29.0 (20) |
| αB13hTEL | Lipofection | 220 (11) | 0 | 83.2 (11) | 8.2 (2) | 0.9 (1) | 7.7 (9) |
| | Microinjection | 180$ (9) | 0 | 63.9 (8) | 21.7 (3) | 1.7 (2) | 13.3 (9) |
| | Total | 400 (20) | 0 | 74.5 (19) | 14.3 (5) | 1.3 (3) | 10.3 (18) |
| MCU-Bsr | Lipofection | 40 (2) | 0 | 58 (2) | 0 | 5 (1) | 38 (2) |
| | Microinjection | 60 (3) | 0 | 55 (3) | 0 | 28 (2) | 17 (3) |
| | Total | 100 (5) | 0 | 56 (5) | 0 | 19 (3) | 25 (5) |

Number of cell lines showing the signals are indicated in parentheses.
\#, 14 cells in 2 cell lines obtained from microinjection contained both the minichromosome and the integration in a single cell.
$, 1 cell obtained from microinjection contained two integration sites in a single cell.

FIG. 19

Stability of the alphoid YAC-derived minichromosome as determined by plating efficiency and by FISH analysis

| Cell line | Days off selection (generations) | Plating efficiency Colony No. on +BS selection / that of off selection | FISH analysis Cell No. showing the signals | | | | | | | |
|---|---|---|---|---|---|---|---|---|---|---|
| | | | Total M cells | Minichromosome/cell | | | Integration site | | | No signal |
| | | | | 1 | 2 | 3 | Tel | Cen | Arm | |
| 7C5HT1 | 0 | - | 50 (%) | 29 (58) | 4 (8) | 1 (2) | 3 (6) | 13 (26) | 0 | 0 |
| | 20 | 630 / 627 (100.4%) | - | | | | | | | |
| | 40 | 634 / 642 (98.7%) | - | | | | | | | |
| | 60 | 655 / 672 (97.4%) | 50 | 30 (60) | 0 | 0 | 1 (2) | 17 (34) | 0 | 2 (4) |
| 7C5HT2 | 0 | - | 50 | 9 (18) | 0 | 0 | 14 (28) | 0 | 0 | 27 (54) |
| 7C5HT3 | 0 | - | 50 | 26 (52) | 6 (12) | 1 (2) | 2 (4) | 15 (30) | 0 | 0 |
| | 20 | 610 / 614 (99.3%) | - | | | | | | | |
| | 40 | 658 / 668 (99.5%) | - | | | | | | | |
| | 60 | 631 / 652 (96.8%) | 50 | 25 (50) | 0 | 0 | 2 (4) | 17 (34) | 0 | 6 (12) |
| 7C5HTm1 | 0 | - | 40 | 14 (35) | 5 (13) | 0 | 1 (3) | 0 | 0 | 20 (50) |
| 7C5HTm3 | 0 | - | 40 | 2 (5) | 0 | 0 | 36 (90) | 0 | 0 | 2 (5) |

Day 0 is the time on which each cell line was established and already had passed 30 to 40 days from the YAC DNA transfections.

FIG. 20

Stability of the alphoid YAC-derived minichromosome (or the integration site) of cell lines recloned from 7C5HT1

| Cell line | Days off selection (generations) | Plating efficiency Colony No. on +BS selection / that of off selection | FISH analysis Cell No. showing the signals | | | | | | | |
|---|---|---|---|---|---|---|---|---|---|---|
| | | | Total M cells | Minichromosome/cell | | | Integration site | | | No signal |
| | | | | 1 | 2 | 3 | Tel | Cen | Arm | |
| 7C5HT1-1 | 0 | - | 50 | 15 (30) | 27 (54) | 0 | 0 | 0 | 0 | 8 (16) |
| | 20 | 633 / 634 (99.8%) | - | | | | | | | |
| | 40 | 1061 / 1031 (103%) | 40 | 6 (15) | 31 (78) | 1 (3) | 0 | 0 | 0 | 2 (5) |
| | 60 | # | - | | | | | | | |
| 7C5HT1-2 | 0 | - | 50 | 46 (92) | 0 | 0 | 0 | 0 | 0 | 4 (8) |
| 7C5HT1-4 | 0 | - | 50 | 41 (82) | 0 | 0 | 0 | 0 | 0 | 9 (18) |
| 7C5HT1-5 | 0 | - | 40 | 32 (80) | 0 | 0 | 0 | 0 | 0 | 8 (20) |
| 7C5HT1-6 | 0 | - | 40 | 31 (78) | 0 | 0 | 0 | 0 | 0 | 9 (23) |
| 7C5HT1-7 | 0 | - | 48 | 39 (81) | 2 (4) | 0 | 0 | 0 | 0 | 7 (16) |
| 7C5HT1-8 | 0 | - | 40 | 32 (80) | 0 | 0 | 0 | 0 | 0 | 8 (20) |
| 7C5HT1-9 | 0 | - | 34 | 0 | 0 | 0 | 0 | 13 (38) | 0 | 21 (62) |
| 7C5HT1-19 | 0 | - | 30 | 0 | 0 | 0 | 29 (97) | 0 | 0 | 1 (3) |

FIG. 21

MAMMALIAN ARTIFICIAL CHROMOSOMES

This application is a continuation of U.S. Ser. No. 09/254,028, filed Sep. 28, 1999, now U.S. Pat. No. 6,297,029, which was the National Stage of International Application No. PCT/JP96/02381, filed Aug. 26, 1996. The entire disclosure of U.S. Pat. No. 6,297,029 is incorporated by reference herein.

TECHNICAL FIELD

This invention relates to mammalian artificial chromosomes (MACs) that can replicate autonomously, can be stably maintained extra-chromosomally and can be transmitted efficiently in mammalian cells. The invention includes methods to construct, modify and stably maintain yeast artifiical chromosomes (YACs) in yeast cells which have the potential ability to form MACs when introduced into mammalian cells.

BACKGROUND ART

Constructing a mammalian artificial chromosome (MAC) carrying the known functional elements required for chromosome replication, stable extra-chromosomal maintenance and segregation in a manipulatable form will be of great value not only for basic studies concerning the organization and function of mammalian chromosomes but also as a vector to introduce DNA segments (genes) of interest to test their functions in mammalian cells or bodies, since the genes carried by MACs will neither be subject to variable expression due to integration position effects nor cause unpredictable insertion mutation in the host chromosomes. Furthermore, a MAC will have the capacity to accommodate a DNA segment having a size in the megabase range, wherein an entire large gene or group of genes and regulatory elements could be included. For these reasons, MACs will offer exciting alternative vectors to currently existing vectors for somatic gene therapy, because frequently used infectious vectors derived from viruses are either integrated randomly into host chromosomes or exist extra-chromosomally but only transiently. Besides, these vectors are able to carry only short DNA segments. A new way to generate transgenic mice will be provided by the invention of MACs, if the stability of MACs during meiosis is established in mammalian development. However, the construction of a MAC has not yet been achieved due to technical difficulties (Willard, Proc. Natl. Acad. Sci. 93, 6874–6850, 1996).

Yeast artificial chromosomes (YACs) has been constructed (Burke et al., Science, 236, 806–812, 1987) with three essential DNA elements from the budding yeast, *Saccharomyces cerevisiae;* namely, an origin of replication or autonomously replicating sequence (ORI or ARS) is required for initiation of DNA replication, telomere sequences (TEL) are required to stabilize and facilitate complete replication of chromosomal ends, and a centromere (CEN) is required for faithful segregation of the sister chromatids after replication. As a result, YACs have become a major tool for cloning large gene segments of complex genomes. Similar to YACs, MACs are believed to be constructable with the three essential elements derived from mammalian genomes. Among the three, telomeres have been isolated from mammalian chromosomes and used for the mammalian chromosome manipulation (Brown et al., Hum. Mol. Genet., 27–1237, 1994; Farr et al., EMBO J., 14, 5444–5454, 1995), but centromeres and the origins of replication for mammalian chromosomes were found to be difficult to isolate because of the unavailability of activity assays.

SUMMARY OF THE INVENTION

The present investigators have analyzed the specific structure of the mammalian centromere locus in order to obtain information concerning the essential functional structure of mammalian centromeres. They have found that centromere protein B (CENP-B), which is one of the antigens recognized by anti-centromere antibodies (Moroi et al., Proc. Natl. Acad. Sci. USA, 77,1627–1631, 1980) at centromeres of various mammalian chromosomes, specifically recognizes and binds the 17 bp sequence (CENP-B box) of the centromere satellite DNA (alphoid DNA) in the human genome (Masumoto et al., J. Cell Biol., 109, 1963–1973, 1989; Muro et al., J. Cell Biol., 116, 585–596, 1992). The recognition sequences of CENP-B were found in centromeric satellite DNA of mouse species (Masumoto et al., J. Cell Biol., 109, 1963–1973, 1989; Kipling et al., Mol. Cell. Biol., 15, 4009–4020, 1995) and the consensus sequence of the CENP-B box was established to be 5'-NTTCGNNNNANNCGGGN-3' (Masumoto et al., NATO ASI Series, vol.H72, Springer-Verlag, 31–43, 1993; Yoda et al., Mol. Cell. Biol.,16, 5169–5177, 1996). They have also demonstrated that a pair of CENP-B sequences form a dimer at the C-terminal and bind to a CENP-B box located in the centromeric satellite DNA at the N-terminal of each CENP-B polypeptide, so that a stable complex, which consists essentially of the dimer protein and the two regions (or strands) of the DNA, was formed (Muro et al., J. Cell Biol.,116,585–596, 1992; Yoda et al., J. Cell Biol., 119, 1413–1427, 1992; Kitagawa et al., Mol. Cell. Biol. 15, 1602–1612, 1995). Further, the investigators studied the location of the CENP-B box in human chromosome 21 (Ikeno et al., Hum. Mol. Genet., 3, 1245–1257, 1994), and found that there are two distinct regions in the alphoid DNA array of human chromosome 21 with regard to the CENP-B box. Specifically, one ($\alpha$21-I) contains a regular series of CENP-B box sequences, and the other ($\alpha$21-II) scarcely contains any CENP-B box sequences, the two regions extend side by side for a stretch of about several megabases, the former is located at a position in the chromosome where the centromere proteins are located and the latter is located at a position slightly shifted towards the short arm of the chromosome (Ikeno et al., Hum. Mol. Genet., 3, 1245–1257, 1994).

The present investigation relates to the DNA region within the CENP-B box. It is an object of the investigation to provide artificial chromosomes derived from the above region that can be stably maintained in the extra-chromosomal region of mammalian cells, especially in human cells, and can be safely transmitted to cells of succeeding generations. The present investigation includes development of methods to construct, modify and stably maintain the precursors of such artificial chromosomes in yeast cells as YACs, which have the potential ability to form mammalian artificial chromosomes when introduced into mammalian cells.

This invention has been achieved by using homologous recombination in yeast cells to determine a method for constructing a yeast artificial chromosome construct comprising a DNA sequence including CENP-B box sequences from the alphoid DNA region of human chromosome 21 that can interact with CENP-B or the centromere protein B, and a segment of the human telomere sequence. Further, the invention involves the determination that when the construct is introduced into a human cell, the construct is replicated autonomously in a human cell and is stably maintained in the cell lineage.

This invention provides a DNA construct comprising a mammalian telomere and a centromere, wherein the centromere has a DNA sequence containing a plurality of copies of the CENP-B box sequence consisting of:
5'-NTTCGNNNNANNCGGGN-3',
wherein N is any one of A, T, C and G.

In a preferred embodiment of this invention, a DNA construct comprises a mammalian telomere and a centromere, wherein the centromere has a DNA sequence containing a plurality of copies of the CENP-B box sequence designated herein as sequence No. 1.

Preferably, the centromere contains spaced repeats of the CENP-B box sequence.

This invention provides a DNA construct comprising a mammalian telomere and a centromere, wherein the centromere has a DNA sequence containing a plurality of copies of the sequence designated as sequence No. 2 or a sequence derived from sequence No.2 in which one or more nucleotides are added, deleted and/or replaced.

In a preferred embodiment of this invention, the centromere is derived from a human chromosome. The DNA construct further comprises one or more sequences necessary for the DNA construct to multiply in yeast cells. The DNA construct further comprises a sequence encoding a selectable marker gene. The DNA construct is capable of being maintained as a chromosome in a transformed cell with the DNA construct. Preferably, the DNA construct is capable of being maintained as a chromosome in a human cell. Further, the DNA construct is capable of being maintained as a chromosome in a mouse cell.

This invention provides a host cell transformed with the DNA construct. In a preferred embodiment, the host cell is a human cell. Further, the host cell is a yeast cell. Still further, the host cell is a mouse cell.

This invention provides a DNA construct that further comprises the sequence of a gene of interest. The DNA construct further comprises a genome DNA sequence containing a structural region and its regulatory region.

This invention provides a method of homologous recombination comprising the steps of:

(i) producing a recombinant DNA construct in a DNA recombination deficient host cell, wherein the host cell comprises a plasmid for DNA recombination and the recombinant DNA construct is prepared from two or more linear and/or circular DNA sequences that are partially homologous, and (ii) collecting cells that carry the recombinant DNA construct but do not carry the plasmid.

This invention, which allows a highly efficient intracellular homologous recombination can simplify conventional in vitro recombination based on the use of restriction enzymes, and thus offers a new recombination method whereby a given DNA segment can be formed. Preferably, the host cell is a yeast cell. Further, the recombinant DNA construct is from a yeast artificial chromosome. Still further, one of the DNA sequences is from a yeast artificial chromosome. Additionally, one of the DNA sequences is from a yeast artificial chromosome which has a repetitive DNA sequence.

This invention provides a method of making a yeast artificial chromosome construct comprising the steps of:

(i) producing a first recombinant yeast artificial chromosome having a mammalian telomere and a centromere in a DNA recombination deficient host cell having a plasmid for DNA recombination, wherein the centromere has a DNA sequence containing a plurality of copies of the CENP-B box sequence consisting of:
5'-NTTCGNNNNANNCGGGN-3',
wherein N is any one of A, T, C and G.

(ii) selecting cells carrying the first recombinant yeast artificial chromosome, but not carrying the plasmid.

(iii) producing a second recombinant yeast artificial chromosome, using the telomeres and the centromere from the first recombinant yeast artificial chromosome in the host cell having a plasmid for DNA recombination, and (vi) selecting cells carrying the second recombinant yeast artificial chromosome, but not carrying the plasmid.

This invention provides a method of producing a mammalian artificial chromosome comprising the step of:

introducing a DNA construct comprising a mammalian telomere and a centromere into a mammalian cell, wherein the centromere has a DNA sequence containing a plurality of copies of the CENP-B box sequence consisting of:
5'-NTTCGNNNNANNCGGGN-3',
wherein N is any one of A, T, C and G.

Further, the mammalian cell is a human cell. Further, the mammalian cell is a mouse cell. Still further, the DNA construct is derived from the *Saccharomyces cerevisiae* α7C5hTEL that has been designated as FERM BP 5625.

This invention provides a mammalian artificial chromosome which is produced according to the method of producing a mammalian artificial chromosome of this invention.

This invention provides a method of fragmenting a chromosome comprising of step of:

introducing a first DNA construct comprising a mammalian telomere, a centromere and a DNA sequence that is partially homologous to the chromosome and a second DNA construct comprising a mammalian telomere and a DNA sequence that is homologous to the chromosome into the mammalian cell, wherein the centromere has a DNA sequence containing a plurality of copies of the CENP-B box sequence consisting of:
5'NTTCGNNNNANNCGGGN3',
wherein N is any one of A, T, C and G.

BRIEF DESCRIPTION OF THE DRAWINGS

The patent or application file contains at least one drawing executed in color.

FIG. 3 shows alphoid DNA inserts which were cloned into YAC55pkc from WAV17 containing human chromosome 21.

FIG. 4(*a*) shows cloned alphoid DNA inserts using PFGE (stained with EtBr).

FIG. 4(*b*) shows the analysis of cloned alphoid DNA inserts by Southern hybridization using an α21-I probe.

FIG. 19 shows the efficiency of mini-chromosome formation by alphoid YAC DNA transfections.

FIG. 20 shows the stability of the alphoid YAC-derived mini-chromosome as determined by plating efficiency and by FISH analysis.

FIG. 21 shows the stability of the alphoid YAC derived mini-chromosome (or integration site) of cell lines recloned from 7C5HT1.

FIG. 25 shows mitotic segregation of mini-chromosome in 7C5HT12.

DETAILED DESCRIPTION OF THE INVENTION

Figure 1:
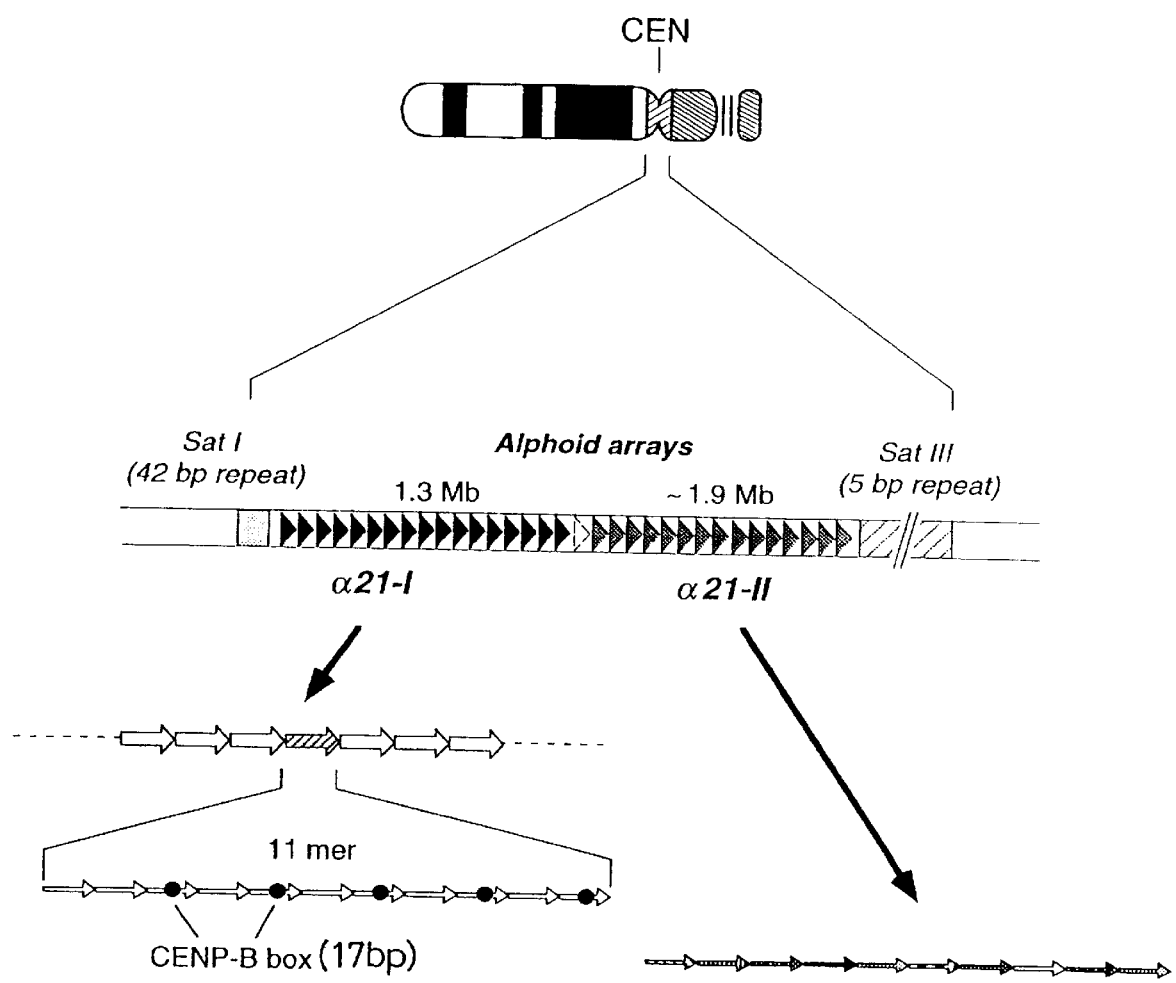
FIG. 1 shows a schematic representation of the centromere region of human chromosome 21. The α21-I locus is composed of 11 monomer order repeat units containing five CENP-B boxes. The α21-II locus on the short arm side of α21-I is composed of diverged alphoid families and may contain other repetitive DNA sequences. CENP-B boxes are distributed regularly in the α21-I locus. On the other hand, the α-21-I locus contains only a few CENP-B boxes.

In the following description, reference will be made to various methodologies that are well known to those skilled in the art of recombinant genetics. Publications and other materials setting forth such well known methodologies will be referred to in the course of this description, and are incorporated herein by reference.

This invention provides a DNA construct that contains a centromere and a mammalian telomere. The DNA construct can be maintained as a chromosome. Even a long DNA fragment, by being inserted into the DNA construct of this invention, can be cloned in mammalian cells or other cells, and allowed to stably express itself.

Centromere

The centromere of this invention has a DNA sequences containing a plurality of copies of the CENP-B box sequence consisting of:

5'-NTTCGNNNNANNCGGGN-3', wherein N is any one of A, T, C and G (Masumoto et al., NATO ASI Series, vol.H72, Springer-Verlag, pp31–43, 1993; Yoda et al., Mol. Cell Biol., 16, 5169–5177, 1996). Further, the CENP-B box sequence is a 17 bp sequence designated as sequence No. 1. The sequence is derived from human chromosome 21 (Ikeno et al, Human Mol. Genet., 3, 1245–1257).

The centromere of this invention has spaced repeats of the CENP-B box sequence. The centromere has copies or repeats of the CENP-B box sequence in sufficient quantity to provide a centromere property to a DNA construct in a host cell. Preferably, the centromere has a region where the CENP-B box sequence is contained in high frequency.

A DNA sequence with regular repeats of the CENP-B box sequence, which is located in a centromere region of the human chromosome contains long repeats as an 11 MER unit. Each 11 MER body has a size of approximately 1900 bp, and each monomer (approximately 170 bp) contains five spaced repeats of the CENP-B box sequence (Ikeno et al, Human Mol. Genet., 3, 1245–1257).

One of the 11 MER bodies in human chromosome 21 has been isolated, sequenced and designated as sequence No. 2 (Ikeno et al, Human Mol. Genet., 3, 1245–1257).

It is to be noted that the centromere has a DNA sequence containing a plurality of copies of the sequence designated as sequence No. 2 or a sequence derived from the sequence No. 2 in which one or more nucleotides are added, deleted and/or replaced.

Further, dimers comprising a part of this 11 MER body or another 11 MER body were isolated, sequenced and designated as sequence No. 3, No. 4, No. 5, No. 6 and No. 7 (Ikeno et al, Human Mol. Genet., 3, 1245–1257).

Cloning of the Centromere

The centromere having the CENP-B box sequences was prepared from human cells, from hybrid cells containing only specific human chromosomes such as WAV 17, or from other mammalian cells.

In a preferred embodiment, a suspension of such cells in PBS is mixed with LMP agarose solution in PBS, to solidify the cells as plugs. The plugs are treated with a proteinase, EDTA and lauroyl-sarcosine, and purified by dialysis to produce agarose plugs of concentrated human DNA. Then, the plugs are treated with restriction enzymes, such as Bgl I, Bgl II and Bam HI, and subjected to pulsed field gel electrophoresis (to be referred to as "PFGE" hereinafter) to remove DNA fragments of 50 kb or less. The remaining plugs are recovered, treated further with Msp I, and dissolved to make a solution. The resulting DNA solution is subjected to dialysis for purification.

After dialysis, the concentrated DNA is inserted into YAC vectors, each vector having a marker, the resulting YACs are fractionated by PFGE, and agarose blocks containing DNA fragments of 50 kb or more are collected. Other methodologies are also useful in the DNA extraction and purification procedure.

The DNA fragments (YACs) extracted from the agarose blocks are mixed with yeast cells lacking DNA recombination enzymes that have been converted to spheroplasts so that the YACs may be introduced into the yeast cells. The yeast cells are grown in culture under conditions that allow the transformed cells to be selected. The use of yeast strains lacking DNA recombination enzymes ensures stable maintenance of the YACs in the transformed cells.

In order to select the centromere DNA sequence having the CENP-B box sequences from among the transformed cells, a CENP-B box sequence, either the entire 11 MER body sequence or a part of the 11 MER body sequence, or the entire 2 MER body sequence or a part of 2 MER body sequence is made into a probe and hybridized with colonies or the DNAs extracted from transformed cells. This procedure enables the isolation of transformed cells having the CENP-B box sequences of a human chromosome.

The centromere DNA sequences which hybridize with the probes form a part of the alphoid region of human chromosome 21, which has been designated by the inventors as the α21-I region or other alphoid region of mammalian chromosomes.

The α21-I region essentially consists of repeats of the 11 MER body, the length of which is approximately 1.3 Mb. This region can be readily extracted from the genome DNA of WAV 17, which is a mouse-human hybrid cell containing human chromosome 21 as the only genetic material of human origin.

The other alphoid region of human chromosome 21 contains a very limited number of CENP-B box sequences or no CENP-B box sequence. The DNA sequence of this region can be selected in a similar manner as described above: human genomes are treated with appropriate restriction enzymes, desired DNA fragments are collected by PFGE and introduced into YACs, the YACs are introduced into yeast cell strains lacking DNA recombination enzymes, α(Y)a and α(Y)b sequences are used as primers and multiplied by PCR, and the PCR products are hybridized with DNA extracted from the yeast cells so that the DNA sequence of interest is detected and cloned. The DNA sequence thus cloned does not contain the above DNA sequence having the repeats of the CENP-B box sequence or the DNA segment that can be detected using the 11 MER body or the 2 MER body as a probe.

The sequence constitutes a part of the alphoid region of human chromosome 21, and is designated by the inventors as α21-II. This sequence is located close to the α21-I region, but more towards the short arm of the chromosome (Ikeno et al, Human Mol. Genet., 3, 1245–1257).

The α21-II region can be readily extracted from WAV17 cells in the same manner as α21-I.

Mammalian Telomere

A mammalian telomere sequence is intended to be the DNA sequence that contains the repetitive sequences located in telomeres or terminal sequences of mammalian chromosomes. To construct a DNA construct that will act as a mammalian chromosome, it is preferable to use a DNA sequence having repeats of the 5'-TTAGGG-3' sequence or a repetitive unit of the human telomeres.

DNA Construct

A DNA construct containing a centromere having the above-described CENP-B box sequences and a mammalian telomere can be maintained stably as a chromosome in a transformed mammalian cell carrying the DNA construct. In other words, it can replicate autonomously in mammalian cells and be maintained stably extra-chromosomally and transmitted to progeny cells. The CENP-B box sequence is preserved among human and other mammals, including mouse and apes (T. Haaf et al J. Mol. Evol., 41: 487–491). In addition, human chromosome 21 is maintained stably in a mouse-human hybrid cell WAV17. Accordingly, when the DNA construct comprising a centromere having the CENP-B box sequence of the invention is introduced into a mammalian cell, it is maintained as a chromosome in the mammalian cell regardless of the origin of centromere.

Preparing the DNA Construct

To prepare a DNA construct by homologous recombination in a host cell, it is necessary that the host cell is competent for homologous recombination and also able to stably maintain the recombinant DNA. The latter requires conditions defective in DNA recombination. Thus, the homologous recombination in this case consists of the following processes: allowing a plasmid carrying the gene for the DNA recombination to be maintained temporarily in the DNA recombination deficient host cell (The plasmid expresses the DNA recombination enzyme while it exists in the host cell), thereby producing recombinant DNA through transient homologous recombination, and then selecting cells that carry the recombinant DNA, but do not carry the plasmid.

DNA Recombination Deficient Host Cell

DNA recombination deficient host cells of the invention include eukaryotic cells including mammalian cells and yeast cells, and bacterial cells. Preferably, the cells are yeast cells. Further, cells lacking one or more DNA recombination enzymes are used in this invention as the host cell. A host cell having a plasmid carrying the gene for DNA recombination is a host cell for the homologous recombination, and a cell that does not carry the plasmid is a host cell for maintaining the recombinant DNA construct, which is a stable provider of the recombinant DNA.

Yeast cells lacking DNA recombination enzyme to be used in this invention include variants lacking the gene rad 51 or rad 52, or the gene coding for the expression of DNA recombination enzymes, or other variants that lacks the genes responsible for the expression of DNA recombination enzymes. Particularly, *Saccharomyces cerevisiae* EPY305–5b strain (provided by Dr. Resnick, NIEHS, USA) or the strain carrying rad 52⁻ are mentioned as a recommended materials for this invention.

The Plasmid for Carrying the Gene for DNA Recombination

The plasmid expresses the DNA recombination enzyme for the homologous recombination in the host cell. When the plasmid responsible for DNA recombination is not evenly distributed to daughter cells during cell division, it is capable of temporarily expressing the DNA recombination enzyme.

The plasmid includes, for example, YpSPL1 (Adzuma et al., Mol. Cell. Biol. 4, 2735–2744, 1984) (provided by Dr. T. Ogawa National Institute of Genetics, Japan) or the plasmid responsible for the expression of RAD52, and YpSL1-Ura. The latter is produced in the following manner: YpSL1 is cut with Eco RV, the 0.57 kb Eco RV fragment (containing a part of the TRP1 gene) is replaced with a Sal I-Xho I fragment (containing the URA 3 gene) of pYAC 55 which has undergone blunt end ligation. Other plasmids having the same functions in the host cell can be used for this invention.

The plasmid to be used in this invention should preferably contain a selectable marker depending on which one can recognize whether a given cell contains the plasmid or not.

The plasmid of this invention signifies a genetic factor which can replicate autonomously and extra-chromosomally in the host cell.

Recombinant DNA

The recombinant DNA constructed by means of homologous recombination should be autonomously replicated and stably maintained in extra-chromosomally in the host cells. Consequently, when the recombinant DNA is constructed in yeast cells through homologous recombination, the recombinant DNA should act as a yeast artificial chromosome which is autonomously replicated and maintained stably in yeast cells.

The recombinant DNA preferably contains a selectable marker that allows transformed cells to be selected under a specific condition.

DNA Sequence for Recombination

One DNA sequence to be introduced into host cells should be partially homologous to one of the other DNA sequences to be introduced. Homologous recombination takes place between the two sequences.

The DNA sequence for recombination can be linear and/or circular. DNA sequences can homologously recombine in each form.

Each DNA sequence for recombination is designed such that the recombinant DNA formed by homologous recombination in cells are replicated autonomously in the host cells and are stably maintained extra-chromosomally. If the cells are yeast cells, the recombinant DNA should have a telomere sequence, an autonomously replicating sequence (ARS) and a centromere (CEN). Thus, the DNA sequence to produce the recombination DNA should contain these three segments, so that after the homologous recombination, the recombinant DNA is produced to function as a yeast artificial chromosome.

For example, in order to produce a yeast artificial chromosome from two DNA sequences, a yeast artificial chromosome is used as one DNA sequence and the other is produced having a telomere sequence at the 3'-terminal or the 5'-terminal and sequences that are homologous to the yeast artificial chromosome. Then, the 3'-terminal or the 5'-terminal of the yeast artificial chromosome is replaced with the other DNA sequence.

Further, the 3'-terminal and the 5'-terminal of a yeast artificial chromosome may be replaced with a DNA sequence having telomere sequences at the 3'-terminal and a DNA sequence having telomere sequences at the 5'-terminal, respectively.

The DNA sequence for recombination carries the DNA sequence of a gene of interest. After the homologous recombination, the recombinant DNA will contain the DNA sequence of the gene of interest.

Particularly, when the DNA sequence for recombination contains a long DNA sequence of the gene of interest, such homologous recombination would be beneficial. If a conventional method is used, it is very difficult to construct a recombinant DNA in vitro having a long DNA sequence using restriction enzymes. However, this intracellular homologous recombination technique can readily produce a recombinant DNA having a long DNA sequence. Further, this intracellular homologous recombination technique allows the recombinant DNA to be stably maintained in host cells. For example, the long DNA sequences include a mammalian genome DNA sequence containing structural gene and its regulatory gene, and a repetitive DNA sequence.

More preferably, the DNA sequence for recombination has a repetitive DNA sequence of the gene of interest. When the DNA sequence contains such a repetitive sequence, the repetitive sequence is readily modified in the host cell which express the functional DNA recombination enzyme. However, this intracellular homologous recombination makes it possible for the DNA sequence with such a repetitive sequence to be recombined appropriately. The resulting recombinant DNA can be maintained stably in the yeast cell without the recombination enzyme. Such a repetitive DNA sequence is located in mammalian chromosomes.

Further, using this homologous recombination method, the resulting recombinant DNA having a long DNA sequence or a repetitive DNA sequence can be modified appropriately and maintained stably in the host cell.

The DNA sequence should preferably contain a selectable marker by which cells with the recombinant DNA are selectively recovered.

Yeast Artificial Chromosome

A yeast artificial chromosome (YAC), which is used as a DNA sequence for recombination and a YAC constructed using homologous recombination according to this invention are intended to mean a DNA fragment which can satisfy at least following two requirements. Specifically, the YAC must replicate autonomously in yeast cells and the YAC must be maintained in the extra chromosomal space of the yeast cell. Accordingly, a YAC contains telomeres, an autonomously replicating sequence, a centromere, and a sequence necessary for initiating replication. Further, these elements are arranged in an effective way. In addition Besides, various other YACs that are well known among those skilled in the art can be utilized.

YAC for DNA Sequence for Recombination

A YAC is a useful tool for DNA recombination. A YAC containing a DNA sequence of a gene of interest is maintained stably in a yeast cell. Preferably, a YAC is used as a DNA sequence for recombination with a long DNA sequence or a repetitive DNA sequence. A YAC should be preferably furnished with a selectable marker which allows selective collection of the transformed yeast cells containing the YAC undergoing homologous recombination.

Figures 5, 6:
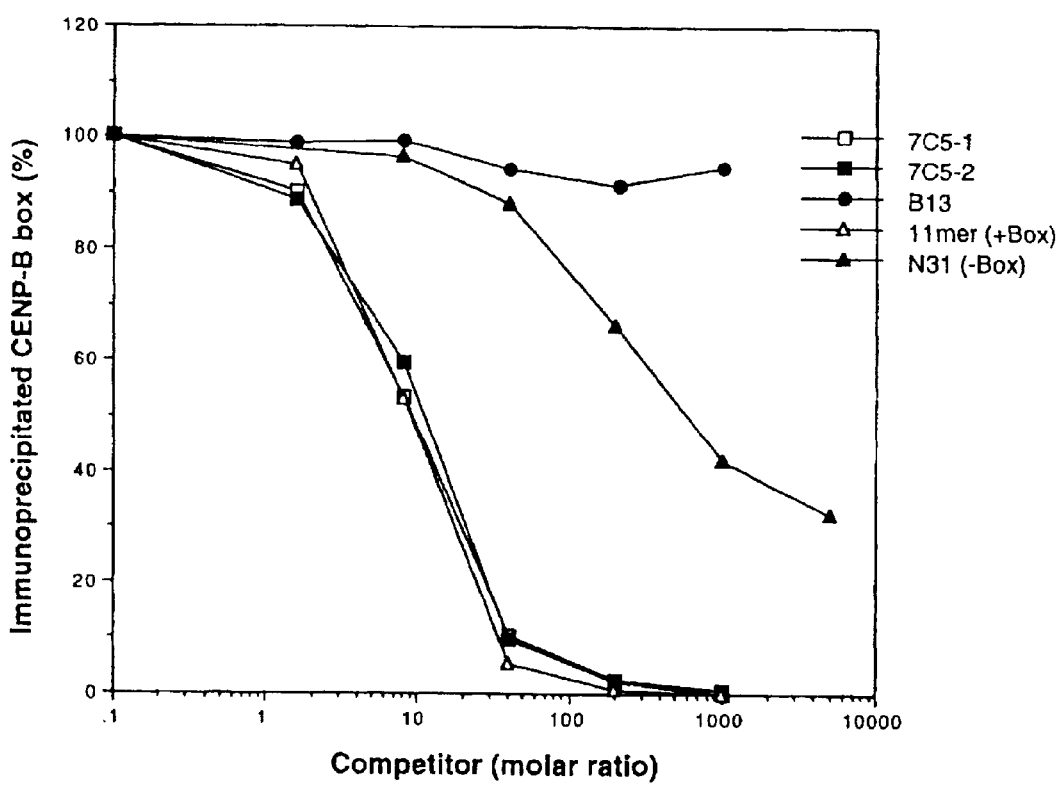
FIG. 5 shows the alphoid length and detection of other repetitive sequences in alphoid YAC clones by Southern and dot hybridization.
FIG. 6 shows a CENP-B box immuno-precipitation competition analysis. PCR generated alphoid DNA from alphoid YAC clones was mixed with end-labeled CENP-B box DNA and CENP-B, then immuno-precipitation reactions were carried out. The ratio (%) of immuno-precipitated probe was plotted against the amount of competitor.

The YAC vector plasmid that is particularly useful with this invention is pYAC 55pkc or a derivative of pYAC 55 (provided by Dr. Olson, University of Washington). pYAC 55pkc can be prepared as shown in FIG. 6. pYAC 55 is cleaved at Cla I with Cla I and is allowed to have blunt ends. Then, it is allowed to undergo self-ligation in the presence of T4 DNA polymerase. A DNA sequence having Not I sticky ends, and Pst 1 (Bst XI), Kpn I, and Cla I positions is inserted into above the plasmid at its Not I positions, in order to produce pYAC 55pkc. This plasmid has cloning sites at Not I, Pst I(Bst XI), Kpn I and Cla I positions. This plasmid, after being completely digested with Bam HI, produces the YAC that is used in this invention. In the alternative, this plasmid, after being completely digested with Bam HI and Cla I, provides the left and right arms of YAC. These left and right arms are utilized for preparation of the YAC to be used for cloning a DNA segment having the gene of interest.

Homologous Recombination in Cells

The DNA recombination deficient host cell which contains the plasmid carrying the gene for DNA recombination extra-chromosomally and is not evenly distributed to daughter cells after cell division, should be preferably prepared by introducing a plasmid into the host cell. Using YAC as the DNA sequence for the recombination, the host cell for homologous recombination should preferably be prepared as follows:

the yeast host cells are transformed by introduction of YAC, and then the plasmid is introduced into the transformed cell.

In particular, when the plasmid is introduced, a DNA sequence for recombination should preferably be introduced concurrently. Such concurrent introduction of the two DNA sequences dispenses with the need for the collection of host cells having expressed DNA recombination enzymes, thus making homologous recombination more efficient.

Introduction of the plasmid, or the plasmid and the DNA sequence into yeast cells can take place by various known methods including the usage of $LiCl_2$ or $Li(CH_3COO)_2$.

As described above, homologous recombination takes place between the DNA sequences in cells containing the plasmid to produce the recombinant DNA.

Selection of Cells Capable of Stably Maintaining the Recombinant DNA

For the recombinant DNA to be maintained stably in cells, it is necessary to select the cells carrying the recombinant DNA but that do not carry the plasmid. This selection takes place by appropriately combining multiple selection markers: the markers contained in the recombinant DNA, the markers removed by the removal of the plasmid and the markers removed from the DNA sequence by the homologous recombination. In the cells selected using the above processes, the recombinant DNA can be maintained stably.

Modifications Added to the DNA Construct

Various modifications can be added to the DNA construct having a minimum necessary length of DNA segments, and the resulting construct can be used as a vector to be utilized for mammalian cells and other cells.

For example, such a DNA construct is made to contain a certain DNA sequence encoding a marker which allows transformed cells to be selected under a specific condition. The selectable marker includes DNA sequences relating to a certain drug resistance or certain nutrition requirements. When the DNA construct is made to contain a DNA segment with such a selectable marker, the transformed cells containing the DNA construct can be selectively collected under conditions in which a selectively acting chemical or chemical is present or absent. Such selectable markers are well known among those skilled in the art, and they can choose appropriate markers according to the DNA constructs to be used, based on commonly understood knowledge.

It should be noted here that, because the DNA construct of this invention is grown in mammalian cells, the marker must function in mammalian cells.

Further, the DNA construct can contain one or more DNA sequences which allow the DNA construct to replicate autonomously in cells other than mammalian cells. Such DNA sequences allow the DNA construct to act as a chromosome in the cell. Accordingly, the DNA construct having such a DNA sequence can act as a shuttle vector for mammalian cells and cells other than mammalian cells, including yeast cells and bacterial cells. The DNA sequence that is necessary for a chromosome to be autonomously replicated in yeast cells or bacterial cells is well known among those skilled in the art.

When cells, which are not mammalian cells and which have been transformed with the DNA construct, are selectively collected, the selectable marker must function in those cells which are non-mammalian cells. Such markers are well known among those skilled in the art, and they can be used appropriately by such persons skilled in the art.

Further, the DNA construct can contain DNA sequences which are necessary for expression of inserted foreign genes. Such DNA sequences allow the artificial chromosome to act as a vector that is necessary for expression of the gene of interest in mammalian cells.

The DNA sequences which are necessary for expression of the gene of interest in various types of cells are well known among those skilled in the art, but they should preferably include at least a promoter sequence and a poly-A sequence, provided that the gene of interest should be expressed in mammalian cells.

Further, the DNA construct can contain a genome DNA sequence comprising a structural region and its regulatory region. In this case, a product derived from the structural region is expressed appropriately in transformed cell according to its regulatory region.

Preparation of a DNA Construct with the Centromere

In particular, to produce the DNA construct comprising a mammalian telomere and a centromere having a DNA sequence containing a plurality of copies of the CENP-B box sequence using homologous recombination, a YAC having the DNA sequence with the CENP-B box sequence is used as the DNA sequence for recombination. This invention comprises two recombination steps.

Another DNA sequence (the first arm) necessary for homologous recombination is allowed to contain on one end of the YAC at least a DNA sequence which is homologous to a DNA sequence located on one end of the above-described YAC, a mammalian telomere, and one or more DNA sequences that are necessary for proper functioning of YAC.

The term "mammalian telomere" has the same meaning as the meaning defined for the newly invented DNA construct.

Further, the DNA sequences necessary for the proper functioning of the YAC on one end of the YAC should contain at least a telomere function in yeast cells. If oen or more of a centromere, ARS or ORI, exist on one arm of the YAC which is to be replaced with the first DNA arm, the sequences should be provided in addition to a telomere.

The first arm should be preferably furnished with a selectable marker by which yeast cells having the first recombinant YAC with this DNA arm inserted can be selectively recovered. Further, the first arm should be preferably furnished with a selectable marker by which mammalian cell having the recombinant YAC construct with this inserted arm can be selectively recovered.

When such first arm is allowed to undergo homologous recombination in the yeast cell carrying the YAC, one arm (one end) of YAC is replaced with this arm, to produce a first recombinant YAC comprising the centromere containing CENP-B box sequences, and a mammalian telomere on one end.

Replacement of the First Recombinant YAC with a Second Arm

In this process, homologous recombination takes place between the first recombinant YAC and a second DNA sequence(a second arm).

When the yeast cell carrying the first recombinant YAC divides itself, the plasmid replicates once during each cell cycle, but it is not distributed evenly to daughter cells. Therefore, appropriate combination use of markers on the YAC and the first arm, and a marker on the plasmid allows selective recovery of yeast cells which contain the first recombinant YAC but not the plasmid.

According to this procedure, the resulting yeast cell that do not contain genes for DNA recombination can maintain the first recombinant YAC stably and even extra-chromosomally. Next, the plasmid is introduced into the YAC thus collected.

A second arm to be used for the second recombination is to replace the other end of the YAC that remains untouched during the first recombination. Similarly to the first DNA sequence, the second arm should be allowed to contain on the other end of the YAC at least a DNA sequence homologous to a DNA sequence located on the other end of the YAC, a mammalian telomere, and DNA sequences that are necessary for the proper functioning of the YAC.

The second arm should be preferably furnished with a selectable marker by which the yeast cells having the second recombinant YAC with this inserted arm can be selectively recovered. Further, the second arm should be preferably furnished with another selectable marker by which the mammalian cells having the second recombinant YAC with this inserted arm can be selectively recovered.

When homologous recombination is allowed to take place in yeast cells thus prepared, a second recombinant YAC is obtained, wherein the other end of the first recombinant YAC is replaced with the second arm, a DNA sequence with CENP-B box sequences is present, and mammalian telomeres are present at both ends.

The second recombinant YAC produced as described above using homologous recombination is also furnished with DNA sequences necessary for it to function in yeast cells. However, if it is inserted into mammalian cells and will be maintained in mammalian cells, those DNA sequences are not always necessary, and can be eliminated.

Furthermore, the recombinant YACs and recombinant DNA construct thus prepared using homologous recombination can be repeatedly subjected to the same recombination process to produce further altered recombinant YACs and DNA constructs.

The Recombinant DNA Construct Transfection into Mammalian Cells

Purified YAC or DNA may be introduced into mammalian cells by the following various methods known in the art. For example, DNA transfections into mammalian cell using lepofectamine(Gibco. BRL) were basically carried out according to the manufacturer's instruction. Then, MAC transfection was carried out by microinjection. Other methodologies are also useful in the present invention.

YAC or DNA constructs introduced into the cells are maintained stably without integrating into host chromosomes, autonomously replicated, and transmitted to their progeny cells.

In other words, a centromere with a plurality of copies of the CENP-B box sequence which is located in the DNA construct of the invention, is apparently a functional centromere. As a result, it is possible to construct vectors for fragmentation of chromosomes. One of the vectors is constructed to combine the centromere of the invention, a sequence homologous with the chromosome for recombination, and a mammalian telomere on one end. The other vector is constructed to combine a sequence homologous with the chromosome, and a telomere on one end. The vectors can be designed to be able to cut the chromosome at a desired position and obtain a fragment of the chromosome which has a desired length. If such designed vectors are used for homologous recombination with the host chromosome in the host cell, a recombinant vector becomes a mini-chromosome, which has a desired fragment of host chromosome, maintained stably in the host cell. Further, this technique of chromosome fragmentation and this YAC technique make it possible to clone a YAC, which comprises such a vector for fragmentation, with a fragment of a mammalian chromosome (mini-chromosome) into a yeast cell. Additionally, the mini-chromosome can be introduced into cells or individuals. These techniques can develop chromosome engineering.

INDUSTRIAL APPLICABILITY

Because the mammalian artificial chromosomes of this invention are replicated autonomously and maintained in mammalian cells, these mammalian artificial chromosomes can act as a vector when a foreign gene is to be introduced into the mammalian cells, and a vector when a foreign gene is to be expressed in the mammalian cells.

This artificial chromosome makes it unnecessary for a gene of interest to be introduced into a native chromosome. That is, mere introduction of the chromosome into the cell leads to transformation. When this artificial chromosome is used as a vector, the gene of interest can be cloned stably; it does not undergo digestion within the transformed cells, and transformation proceeds without the position effects as a result of the gene integration into the host chromosomes. Particularly, this will be beneficial when used as a vector in gene therapy in which it is necessary to transfer normal genes, or genes which control the expression of abnormal genes into affected cells.

BEST MODE FOR CARRYING OUT THE INVENTION

Having now fully described the present invention, the same will be more clearly understood by reference to certain specific examples which are included herewith for purposes of illustration only, and such examples are not intended to be limiting of the invention, unless specified.

Mammalian Cell Lines

WAV17, a mouse-human somatic hybrid cell containing two or three copies of human chromosome 21 per cell as the only human component, was obtained from Dr. F. Ruddle (Yale University, USA) and HT1080, a human male fibroblast cell was obtained from Dr. D. Broccoli (The Rockefeller University). WAV17 and HT1080 were maintained in DME medium (Nissui, Japan) supplemented with 10% fetal calf serum (Bio Whittaker)at 37° C. under 5% CO2.

Antibodies

Anti-centromere antibody (ACA)-positive serum from a scleroderma CREST patient,K.G., which recognizes three major centromere antigens, CENP-A, B and C by immunoblotting analysis with HeLa nuclear extract, was obtained from Dr. Y. Muro (Nagoya University, Japan). The polyclonal antibody against the $NH_2$-terminal region of human CENP-B (BN1) was described previously (Kitagawa et al Mol. Cell. Biol. 15,1602–1612, 1995). Two polyclonal antibodies CGp2 and CRa2 against the COOH-terminal region of human CENP-C were raised by immunizing a guinea pig and a rabbit, respectively, with polypeptides containing residues 630–943 of CENP-C. A plasmid expressing the COOH- terminal region of CENP-C, pETCC630-C, was constructed by cloning a XbaI-BamHl fragment of CENP-C cDNA derived from pCNPCC1, a clone screened from the Okayama Berg library (Okayama et al., Mol. Cell. Biol. 3; 280–289, 1983), to the NdeI-BamHl site of pET3c using a NdeI-XbaI linker (5'-TATGAATCTTGATTGTT-3'). The polypeptides were expressed in *E. coli* cells using pETCC630-C and the T7 expression system (Studier et al., Methods Enz. 185; 60–89, 1990) and purified by the same procedure that was described in Kitagawa et al 1995.

Yeast Strains and Media

The *Saccharomyces cerevisiae* strain EPY305-5b (MATΔ, rad52-Δ2000, leu2-Δ1, lys2, ade2-101, his3-Δ200, trp1:: HisG, ura3-52) was obtained from Dr. M. Resnick (NIEHS, USA) and grown in a rich medium YPD or in a synthetic minimal SD medium. Media and solutions used in examples are described as follows:

YPD: 1% yeast extract, 2% polypeptone, 2% glucose

SCE (for transformation): 1M sorbitol, 0.1M sodium citrate pH5.8, 10 mM EDTA pH8.0

SCE (for agarose plug): 1M sorbitol, 0.1M sodium citrate pH7.0, 50 mM EDTA pH8.0

STC: 1M sorbitol, 10 mM Tris-HCl pH7.4, 10 mM $CaCl_2$

PEG: 20% PEG 8000, 10 mM Tris-HCl pH 7.4, 10 mM $CaCl_2$

Figure 2:
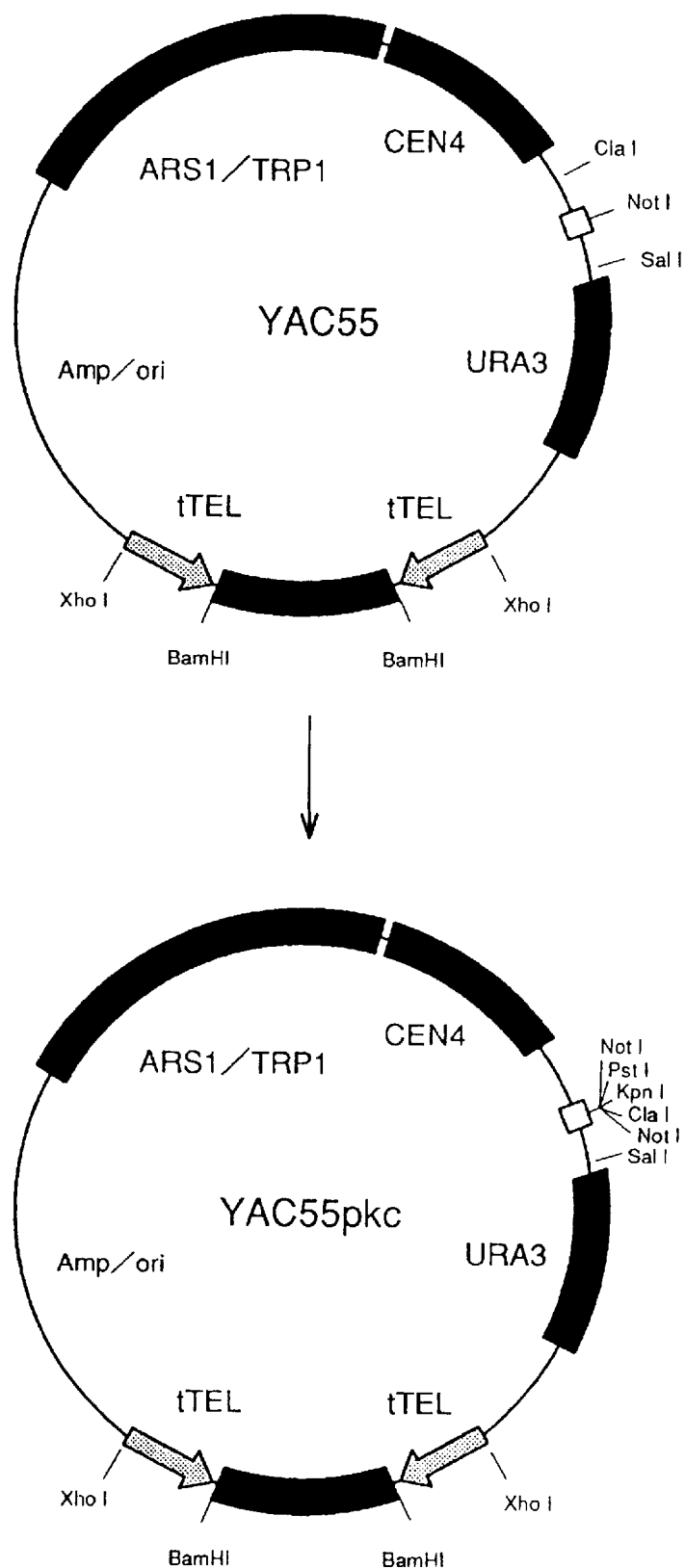
FIG. 2 shows the construction of pYAC55pkc that was used for Alphoid DNA cloning.

SOS (10 ml): 5 ml of 2M sorbitol, 2.5 ml of YPD, 2.4 ml of DW, 70 μl of 1M $CaCl_2$, 100 μl of 100×Uracil SORB plate: 1M Sorbitol, 0.67% yeast nitrogen base without amino acids, 2% glucose, 1.7% bacto agar, 1×amino acids Top agar: 1M sorbitol, 0.67% yeast nitrogen base without amino acids, 2% glucose, 17% bacto agar, 1×amino acids SD: 0.67% yeast nitrogen base without amino acids, 2% glucose, 1×amino acids 10×amino acids: 400 mg/l arginine-HCl, 200 mg/l histidine-HCl, 600 mg/l isoleucine, 600 mg/l leucine, 500 mg/l lysine-HCl, 200 mg/l methionine, 500 mg/l phenylalanine, 500 mg/l tyrosine, 100 mg/l adenine sulfate, 2000 mg/l threonone, 400 mg/l tryptophan, 200 mg/l uracil 100×tryptophan: 4.0 g/l tryptophan 100×uracil: 2.0 g/l uracil 100×lysine: 5.0 g/l lysine Solution I: SCE (for agarose plug) supplemented with 2 mg/ml zymolyase 100T (Seikagaku Corporation) and 33 mM DTT Solution II: 0.45M EDTA pH9.0, 10 mM Tris-HCl pH8.0, 50 mM DTT Solution III: 0.45M EDTA pH9.0, 10 mM Tris-HCl pH8.0, 1% lauroyl-sarcosine, 1 mg/ml proteinase K YAC Vectors and Plasmids Construction of YAC Cloning Vectors YAC vector and pYAC55 pkc used for Alphoid DNA cloning are derivatives of pYAC55 (gifted by Dr. M. V. Olson, U. Washington). A Cla I site of pYAC55 was disrupted by digestion with Cla I and, after the creation of blunt ends, was self-ligated with T4 DNA polymerase. Then, the derivative plasmid was digested with Not I and oligonucleotides containing Pst I(Bst XI), Kpn I, Cla I sites flanked by Not I sites (YL1 and Y L2) were inserted into the Not I site of the derivative plasmid, resulting in the construction of pYAC55 pkc and creating Not I, Pst I (Bst XI), Kpn I, Cla I cloning sites (FIG. 2).

Rad52 Expressing Plasmids

Rad 52 expressing ARS plasmid YpSL1(Adzuma et al., Mol. Cell. Biol. 4, 2735–2744, 1984) was a gift from Dr. T. Ogawa (National Institute of Genetics, Japan). YpSL 1 was digested with EcoRV, and a 0.57 kb EcoRV fragment containing a part of the TRP 1 gene was replaced with a 2.6 kb Sal I-Xho I fragment containing URA3 gene derived from pYAC 55 after the creation of blunt ends with T4 DNA polymerase. The resulting plasmid YpSL1-Ura contained the URA3 gene instead of the TRP1 gene. Oligonucleotides used in this procedure were described as follows:

Y L 1:
5'-GGCCGCCCAATGCATTGGTACCATCGATGC-3'

Y L 2:
5'-GGCCGCATCGATGGTACCAATGCATTGGGC-3'

Preparation of Agarose Plugs

WAV17 cells at a concentration of $8 \times 10^7$ cells/ml in PBS were mixed with an equal volume of 1% solution of Low Melting Point (LMP) agarose (Seaplaque GTG, FMC) in PBS and then distributed into a 100 μl plug former (molds). Solidified agarose plugs were treated with 0.5 M EDTA, 1% lauroyl sarcosine and 10 mg of proteinase K per ml for 24 hrs at 50° C. Just before restriction endonuclease digestion, the agarose plugs were dialyzed against TE (10 mM Tris-HCl pH 7.4 and 0.1 mM EDTA) containing 1 mM PMSF and then against TE. For Southernhybridization sliced agarose plugs of about 8 μl in volume were digested with 20–50 units of restriction endonuclease in the 50 μl mixture (Takara, Japan or NEB) as specified in each experiment.

A yeast strain containing a YAC was inoculated into 50 ml of SD medium (−Ura, −Trp or −Lys, −Trp) and was grown in a flask to late log phase (4 days, at 30° C.). The cells were transferred into a 50 ml Falcon tube and collected by centrifugation at 2000 g for 5 min, and then resuspended and washed with 50 ml of 50 mM EDTA. After the centrifugation and removal of all the supernatant, the cell pellet (about 330 μl) was resuspended with the same volume of Solution I supplemented with 33 mM DTT and 4 mg/ml zymolyase 100T (Seikagaku Corporation) and incubated at 37° C. for 15 min. Then, the cell suspension was mixed thoroughly with the same volume (about 330 μl) of 2% LMP agarose (Seaplaque GTG.) in 0.15M EDTA by pipetting with cut off tip. Using a cut off yellow tip 100 μl aliquots of the mixture were poured into plug formers kept on ice. The agarose plugs were transferred into Solution II and incubated at 37° C. overnight. Then, the buffer was replaced with Solution III and the plugs were incubated at 50° C. overnight. The plugs were stored at 4° C. until use.

Pulse-Field Gel Electrophoresis (PFGE)

PFGE was performed using a pulsaphor electrophoresis unit (Pharmacia) in 1%LE agarose (FMC) and 0.5×TBE (50 mM Tris-HCl, 50 mM Boric Acid and 1 mM EDTA) at 10° C. After ethidium bromide staining and photography, gels were treated with 0.25M HCl for 20 min and transferred to nylon membranes (Hybond N, Amersham) in 0.4 M NaOH overnight.

Southern Hybridization

Hybridization probes were prepared by labeling gel-purified insert fragments of plasmid DNA or PCR $^{32}$P-dCTP using the random primer method. Nylon membranes to which DNA was transferred from the gel of PFGE, were prehybridized and hybridized under conditions of 50% formamide, 4×SSPE, 1% SDS, 0.5% skim milk and 500 μg/ml sonicated salmon sperm DNA and supplemented with or without probe DNA at 42° C. Final washing was performed in 0.1×SSC and 0.1% SDS at 68° C.

Immunoprecipitation-Competition Assay

Complementary oligonucleotides containing the CENP-B box sequence were synthesized chemically.

CB29a:
5'-TCAGAGGCCTTCGTTGGAAACGGGATTTC-3'

CB29b:
3'-CTCCGGAAGCAACCTTTGCCCTAAAGAGT-5'

End-labeled probe DNA was prepared from annealed CB29a and CB29b DNA by repairing the single-stranded ends with Klenow Fragments. End-labeled oligonucleotides (0.5 ng) were mixed with varying amounts of unlabeled DNA and incubated with HeLa 0.5 M NaCl extract (1.5×10$^5$ nuclei) in 100 μl of binding buffer (10 mM Tris-HCl pH 8.0, 10% glycerol, 1 mM EDTA, 2 mM DTT, 150 mM NaCl, 0.05% NP-40, 100 μg/ml poly(dI.dC),poly(dI.dC)) for 1 h at RT. Then, 1 μl of anticentromere serum (K.G.) diluted (1:5) with binding buffer was added to the mixture and incubated for 30 min on ice, After 25 μl of protein A-Sepharose (Pharmacia) was added, the mixture was incubated for 30 min on ice and washed three times with 0.5 ml of binding buffer containing 0.5% NP-40. Finally, the radioactivity of the pellet was determined using a liquid scintillation counter (Beckman).

Preparation of 0.5 M NaCl extracts from interphase nuclei was performed as described by Masumoto et al. (1989, J. Cell Biol. 109, 1963–1973).

PCR

PCR was carried out to amplify various subfamilies of alphoid DNA specific for human α21-I or α21-II using complementary strand primers which were chosen from consensus sequence in alphoid monomers. In the case of tandemly repeated sequences, when complementary strand primers of a conserved motif were used for PCR, various sequences between the motifs in the repeats were amplified. α(1)a/b primers were used to amplify alphoid sequence cloned in α7C5 YAC, and α(Y)a/b primers were used to amplify alphoid sequence cloned in αB13 YAC.

Primer sequences:
α(1)a: 5'-ACAGAAGCATTCTCAGAA-3'
α(1)b: 5'-TTCTGAGAATGCTTCTGT-3'
α(Y)a: 5'-AGAAACTTCTTTGTGATG-3'
α(Y)b: 5'-CATCACAAAGAAGTTTCT-3'

All PCR reactions were carried out in a 50 ml reaction mixture containing 10 mM Tris-HCl pH 8.4, 50 mM KCl, 1.5 MM MgCl$_2$, 0.01% gelatin, 0.2 mM dNTPs and 1 unit of Taq polymerase (Perkin-Elmer) using 1 mM of primers and 1 ng of WAV17 genomic DNA or yeast genomic DNA containing a YAC. 30 reaction cycles were performed, consisting of 30 sec denaturation at 94° C., 90 sec annealing at 55° C. or 57° C. and 60 sec extension at 73° C. PCR products were precipitated with ethanol to remove primers and used as probes.

Fluorescence In Situ Hybridization

Metaphase cells of transformants arrested by colcemid or TN16 (Wako Pure chemical) and interphase cells of HT1080 and derivatives were fixed in methanol/acetate (3:1) and spread on coverslips using a conventional procedure. FISH was carried out according to the method described by Masumoto et al 1989, Exp. Cell Res., 181, 181–196. Biotin-labeled probe was detected with FITC conjugated avidin (1:250 dilution with 4×SSC, 1% skim milk, Vector) and digoxigenin-labeled probe was detected with TRITC conjugated anti-digoxigenin (1:20 dilution with 4×SSC, 1% skim milk, Boehringer Mannheim) by incubation at 37° C. for 1 hr. Chromosomes and nuclei were counter-stained with DAPI.

Simultaneous Detection of FISH and Indirect Immunofluorescence

The simultaneous detection method described by Masumoto et al 1989, Exp. Cell Res., 181, 181–196 was modified as follows. Swollen and PLP fixed cells of transformants were incubated with an anti-CENP-B (BN1) or anti-CENP-C (CGp2) antibody at 37° C. for 1 hr and then washed and incubated with the 2nd antibody, FITC-conjugated anti-rabbit and anti-guinea pig IgG (Bethy Laboratory), respectively. The cells were washed and fixed again with PLP fixative on ice for 30 min and then with methanol/acetate (3:1). After dehydration and air drying, cells on coverslips were denatured with 70% formamide at 70° C. for 30 min and hybridized under the same conditions as described in the following section. Coverslips were washed twice with 50% formamide/2×SSC at 37° C. for 7 min, twice with 2×SSC for 7 min at 37° C., once with 1×SSC at room temperature for 10 min and blocked in 5% skim milk /4×SSC for 1 hr at RT. Signals from YAC arms were simultaneously detected with the signals from CENP-B or CENP-C and TRITC-conjugated anti-digoxigenin, respectively.

Plating Efficiency

The passage of the transformed cells in the condition without selection was analyzed by plating efficiency up to 60 days (about 60 generations). Every 4 days, the cells were plated with new medium without BS at 1:16 dilution. After 20, 40 and 60 days from the start, 1–2×10$^3$ cells were duplicated and plated into medium with and without BS. Colonies were counted after 7–8 days. Non-resistant cells died within 3–5 days.

DNA Probes for FISH

Probes were prepared by the random primer method or by nick translation using labeled dUTP as a substrate. Gel purified 11 MER body described herein as sequence No. 2 (11-4 alphoid DNA) (for detection of the α21-I locus and clones), α(Y)a/b primed PCR products (for detection of α21- II locus and clones), YAC vectors (telomere sequences were removed by Cla I·Kpn I digestion or Cla I–Xho I digestion from the vectors) and a telomere sequence (TTAGGG)n were labeled with biotin-11-dUTP (Enzo Biochem) or digoxigenin-11-dUTP(Boehringer Mannheim). After removal of free nucleotides in the reaction mixture using a Sephadex G-50 spun column, probes were precipitated with ethanol and dissolved in formamide.

EXAMPLE 1

Cloning of Alphoid DNA Arrays from Human Chromosome 21 into YAC

We tried to clone the centromeric alphoid DNA regions into YAC using the rad 52⁻ yeast host, EPY3055b.

One agarose plug (100 μl) containing WAV17 genomic DNA was divided into four pieces and digested completely with Bgl I (60 U), Bgl II (60 U) or Bam HI (72 U) at 37° C. overnight. The reaction was stopped by adding final 50 m M EDTA, the solution was replaced with NDS (0.45M EDTA, 1% lauroyl-sarcosine, 10 mM Tris-HCl pH7.4) and stored at 4° C. The plugs were equilibrated with 1×TBE for 2 hr and loaded on 1% pre-cooled LMT agarose gel. After removing short DNA fragments less than 50 kb by PFGE (90 V, 30 sec.pulse, for 70 to 90 min.), the agarose plugs were recovered from the separation gel. Through these steps, alphoid DNA from human chromosome 21 was concentrated up to 8 to 10 fold as compared with the starting fraction of bulk genomic DNA. The recovered plugs (total 100 μl) were incubated with Msp I digestion buffer for 2 hr to equilibrate the buffer and put in a new buffer. The DNA in plugs were digested partially with Msp I (120 U) at 37° C. for 1 hr and then the reaction was stopped by adding final 5 mM EDTA. After changing the buffer in the gel with 1×TAE supplemented with 50 mM NaCl for 2 hr, all the remaining buffer was removed and the agarose of the plugs was melted at 68° C. for 3 min, then cooled to 42° C. 20 U of agarase (Sigma) was added to the melted solution (100 μl), and the solution was incubated at 42° C. overnight. The DNA in the solution was then concentrated up to 20 folds in the colodion bag (pore size 8 nm, cut off MW 12000, sartorius) by vacuum dialysis against the buffer containing 10 mM Tris-HCl pH7.4, 0.5 mM EDTA pH8.0, 50 mM NaCl, and the concentrated DNA solution was dialyzed again against the same buffer for 4 hr. The concentrated genomic DNA (about 35 μg from 17 initial agarose plugs) was ligated with the same amount of YAC55 pkc right and left arms (42 μl solution and 3360 U ligase). The ligated DNA solution was mixed with gel loading buffer, loaded on pre-cooled 1.2% LMP agarose gel and size fractionated with PFGE at 170V, 8 sec. pulse, for 2 hr and then at 120V, 8 sec. pulse for 18 hr. The agarose block containing the DNA molecules greater than 50 kb in size, estimated by the staining of control marker lanes, were dissected, and the DNA in the gel was used for yeast transformation after the buffer exchange with 1×TAE supplemented with 50 mM NaCl and agarase treatment.

Yeast Transformation with Spheroplast

Yeast colonies (EPY305-5b) on YPD plate were inoculated to 50 ml YPD medium at an OD660 of 0.02, and grown at 30° C. for 14–20 hr until the OD660 reached 1.6–1.8. The cells were transferred to a 50 ml tube, pelleted at 1500 rpm for 5 min at room temperature, and washed once with 25 ml of water and then washed with 25 ml of 1 M sorbitol, and spun again. The cells were re-suspended with 20 ml of SCE and mixed with 40 μl of β-mercaptoethanol. 100 μl of the samples was removed from the suspension and the starting OD800 was determined after diluting with 900 μl of water. The cell suspension was mixed with 100 μl of 2 mg/ml Zymolyase and incubated at 30° C. The incubation was stopped when the OD800 of the sample decreased to 75–80% of the starting value. Then, the spheroplasted cells were pelleted at 950 rpm for 5 min, re-suspended and gently washed twice with 15 ml of STC. The cells were pelleted again and re-suspended in 1 ml of STC. 100 μl each of the spheroplasted cells were mixed gently with 10 μl of the transforming YAC DNA prepared in Example 1, incubated at room temperature for 10 min, then mixed with PEG solution and incubated at room temperature for 10 min. The spheroplasts were pelleted at 950 rpm for 5 min, and the supernatant was removed as much as possible, then re-suspended with 200 μl of SOS and incubated at 30° C. for 30 min. The cells were pelleted and re-suspended with SD(-ura -trp). The suspension was mixed with 7 ml of TOP agar melted at 50° C. and poured onto five melted at 50° C. SORB plates (-ura -trp) pre-warmed at 42° C. The plates were incubated at 25° C. for 5–7 days.

Figures 4A, 4B, 4C:
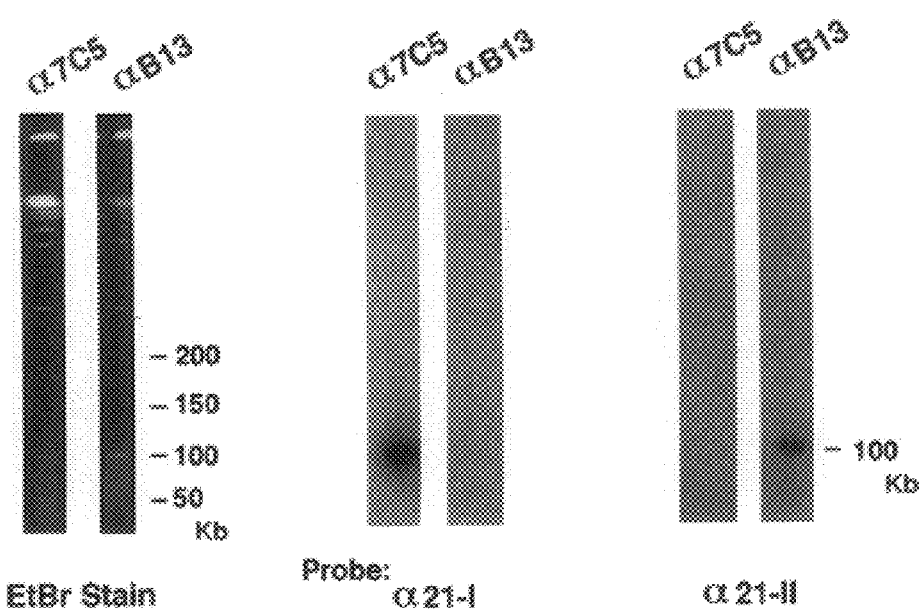
FIG. 4(c) shows the analysis of cloned alphoid DNA inserts by Southern hybridization using an α21-I probe.

YAC libraries were constructed with genomic DNA from the human and mouse somatic cell hybrid (WAV17) containing chromosome 21 as an only human component and about 10000 colonies of the resulting YAC libraries were screened with alphoid DNA probes (an alphoid 11 monomer higher order repeating unit of α21-I and the PCR degenerated α21-II (Ikeno et al Hum. Mol. Genet. 3, 1245–1257, 1994)). We obtained 4 and 7 stable alphoid YAC clones containing the α21I and α21II arrays, respectively. FIG. 3 shows that the YAC clones, α7C5 and αB13 from α21I and α21II array, respectively (FIG. 2), containing the longest insert sizes estimated from PFGE analyses, although the sizes of insert were about 100–110 kb (FIG. 4). These two clones were analyzed by dot hybridization using repetitive DNA probes, restriction digestion and Southern hybridization, PCR analysis of cloned ends and by DNA immuno-precipitation competition assay with CENP-B proteins (FIGS. 4, 5 and 6). The results indicated that α7C5 was composed of rigid tandem repeats of the 11 MER repeating unit and contained CENP-B boxes in very high frequency with all other alphoid monomer units (FIG. 1). In contrast to this clone, αB13 was mostly composed of diverged alphoid DNA and contained about a 2 kb fragment of satellite III sequence on one of its cloning ends, but contained no CENP-B box. αB13 also may contain a small copy of the Alu sequence. Thus, these two YAC clones from the α21-I and α21-II regions represent characteristic alphoid arrays in the chromosome 21 centromere, and they will provide good controls for each other to assay whether these two alphoid sequences have a centromere function or not in human cells.

EXAMPLE 2

Construction of Replacement Vectors

To construct replacement YAC arm vectors, a left arm and a right arm YAC vectors were modified with human telomere sequences. Also, yeast and mammalian selection maker genes (Blastisidine S resistant gene: Bsr, and/or Neomycin resistant gene: Neo) were cloned into the vectors.

A Not I-Cla I fragment containing 600 bp of mammalian TTAGGG telomere repeats (0.6 kb element) from the vector pEND2R (a derivative plasmid of pHUTEL2 (Thesis, Edinburgh University, U.K.) was subcloned in a head to tail arrangement with the 0.8 kb element of pgb4g7 (Thesis, Edinburgh University, U.K.), which contains 0.5 kb of mammalian telomere repeats flanked by 0.3 kb of yeast TG1-3 telomere repeats. An oligonucleotide containing the 18 bp Isce I recognition site (Boehringer) flanked by Bam HI compatible ends was inserted into a Bam HI site located at the junction of the 0.6 kb and 0.8 kb elements. Only one Bam HI site was retained, immediately downstream of the Isce I site. The 0.6 kb element followed by an Isce I site then the 0.8 kb element constitutes the omega cassette.

Figure 7:
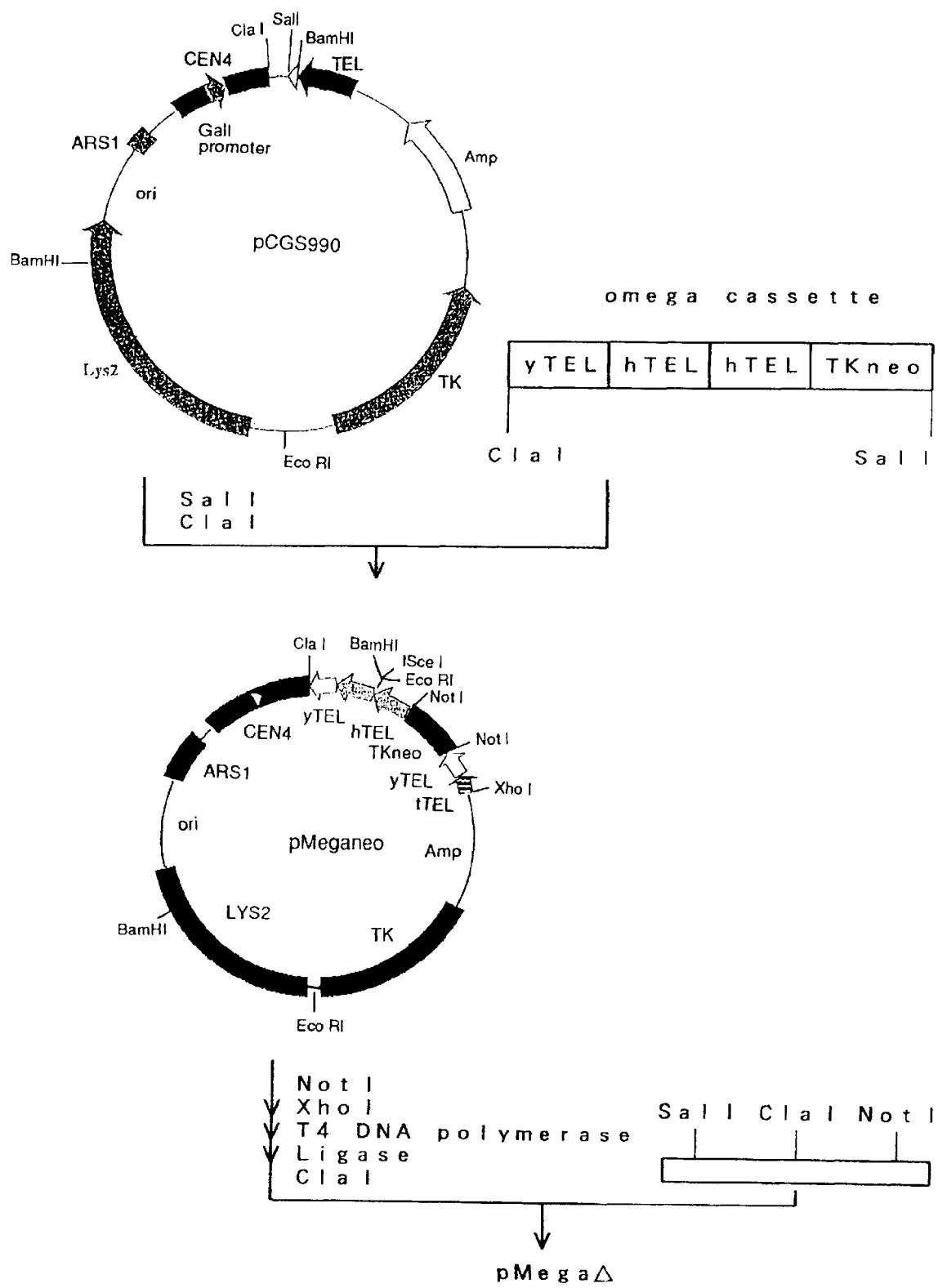
FIG. 7 shows a schematic of the construction of pMegaΔ using pCGS990.
Figure 8:
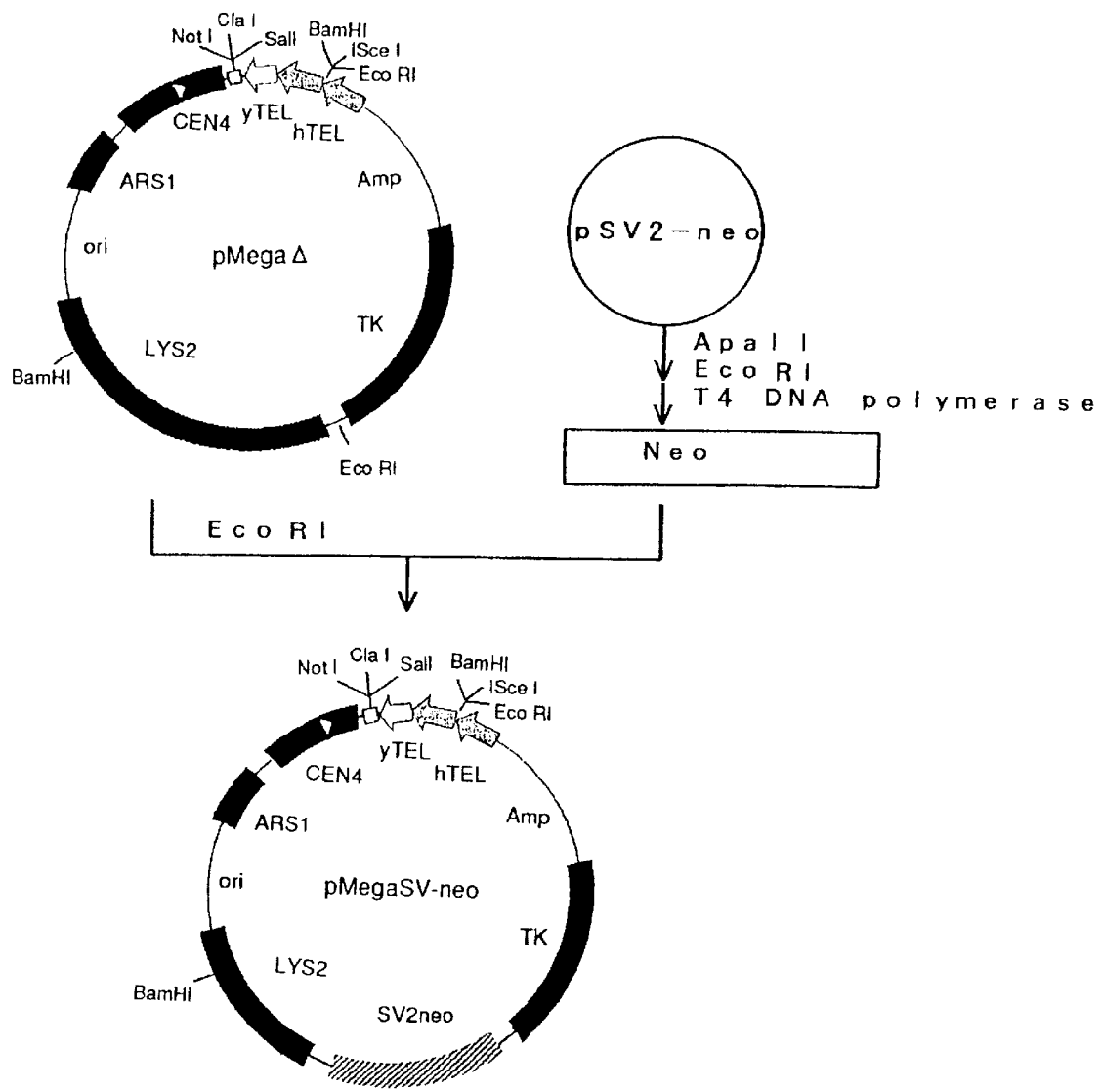
FIG. 8 shows a schematic of the construction of pMega SVneo using pMegaΔ.

The left arm replacement vectors are modified versions of pCGS990 described previously (Smith et al 1993; Mammalian Genome, 4, 141–147). pCG990 was a gift from D. T. Moir, Collaborative Research, Inc. A 2.6 kb Sal I-Cla I fragment which contains a neomycin resistance gene derived from pMC1polA (Stratagene) and a copy of the omega cassette was cloned into Sal I-Cla I digested pCGS990, resulting in the construction of pMeganeo (FIG. 7). Tetra Hymena telomere sequence and the neomycin gene in pMeganeo were removed by Not I complete digestion and XhoI partial digestion and the plasmid was circularized with ligation after the creation of blunt ends using T4 DNA polymerase treatment. Then, oligonucleotides containing Sal I, Cla I and Not I sites flanked by Cla I compatible sites(YL3 and YL4) were inserted into the Cla I site of the derivative plasmid, resulting in the construction of pMegaΔ retaining only one Sal I, Cla I and Not I site (FIG. 8). A 3.6 kb ApaLI-EcoRI fragment containing a neomycin resistance gene derived from pSV2-neo was treated with T4 DNA polymerase and cloned into the partial digested EcoRI site between Lys2 and TK genes of pMegaΔ, resulting in the construction of pMegaSV-Neo (FIG. 8). pMegaΔ or pMegaSV-Neo were used for the replacement of the alphoid YAC left arms by homologous recombination after linearization by Sal I and Not I digestion.

Figure 9:
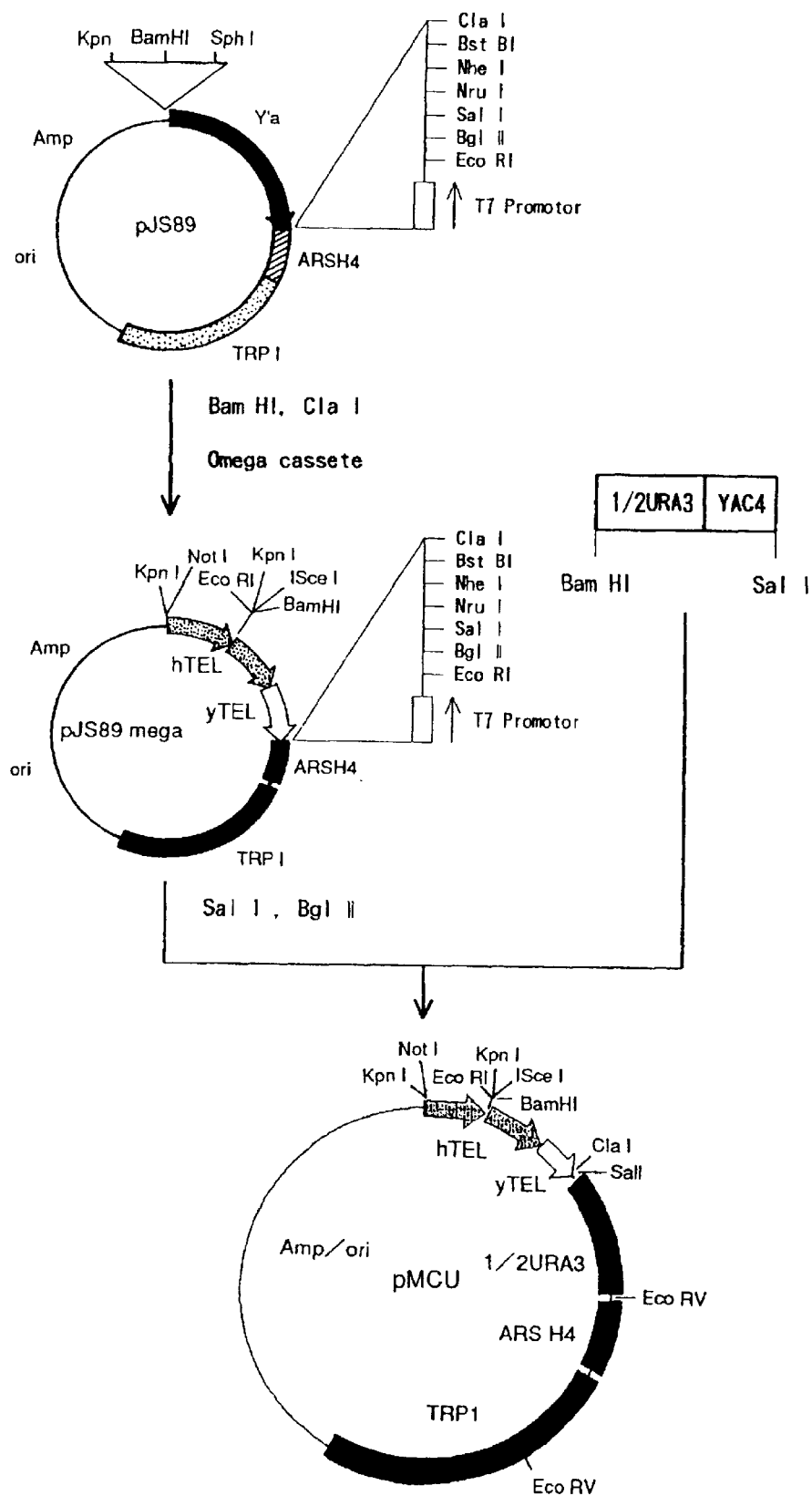
FIG. 9 shows a schematic of the construction of pMCU using pJS89.
Figure 10:
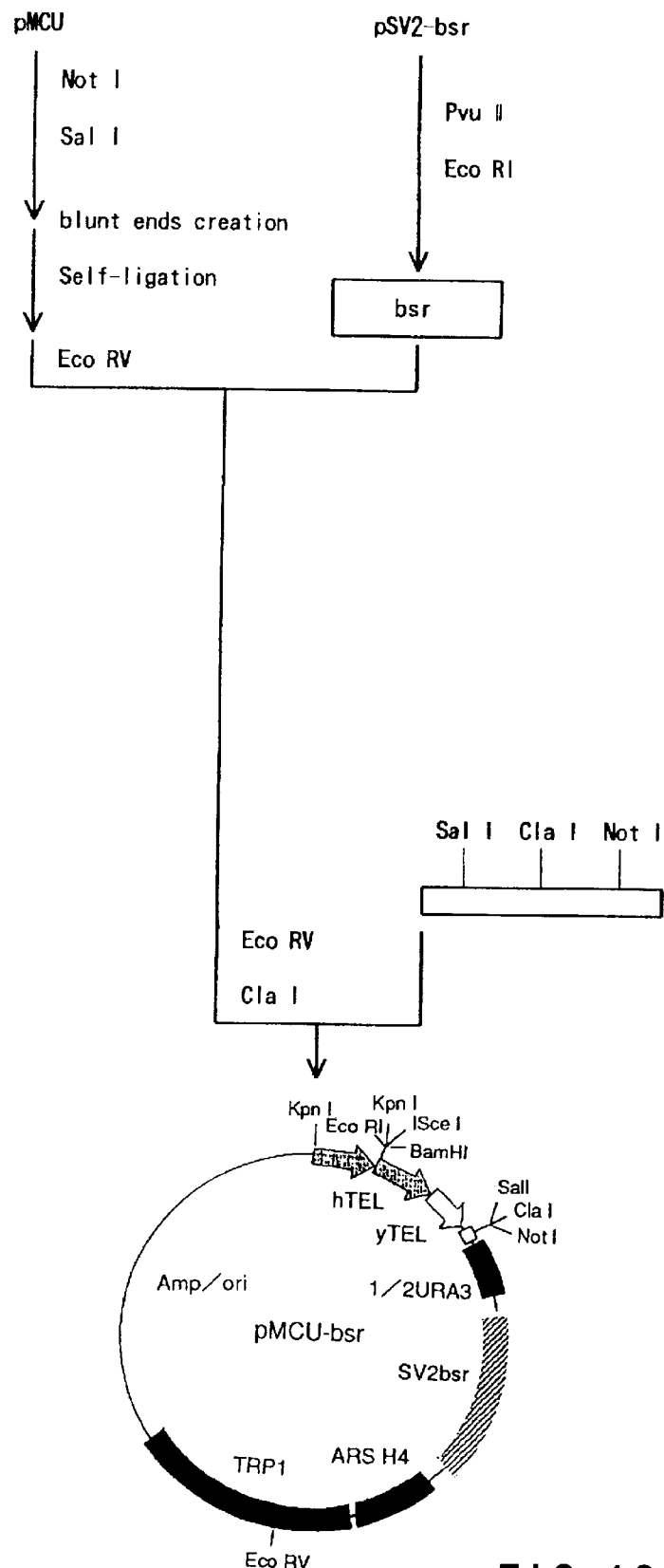
FIG. 10 shows a schematic of the construction of MCUbsr using pMCU.

The right arm replacement vectors are derivatives of pJS89 described previously (Shero et al 1991, Genomics, 10, 505–508). pJS89 was digested with Bam HI and Cla I to delete the Y'a element. Insertion of the omega cassette into Bam HI-Cla I site resulted in the construction of pJS89mega (FIG. 9). A 1.1 kb Sal I-Eco RV fragment (½ ura element) from pYAC 4 containing a truncated (0.42 kb), non functional copy of URA3 gene from the Eco RV site flanked by 0.7 kb of YAC4 sequences up to the Sal I site (Burke et al 1987, Science, 236, 806–812), was subcloned into pBluescript to create pblue ½ ura. The ½ ura element was then subcloned as a 1.1 kb Sal I-Bam HI fragment into Sal I-Bgl II digested pJS89mega resulting in pMega Conversion Ura (pMCU) (FIG. 9). The Not I and Sal I sites of pMCU were disrupted by Not I or Sal I digestion and self-ligation after the creation of blunt ends with T4 DNA polymerase treatment. Then, the plasmid was digested with EcoRV partially and a 2.6 kb Pvu II-EcoRI fragment containing brasticidine S resistance gene derived from pSV2-Bsr (Kaken seiyaku) was cloned into the one of EcoRV sites between ½ URA and ARS H4 genes of pMCU derivative. Finally, oligonucleotides containing Sal I, Cla I and Not I sites flanked by Cla I compatible sites (YL3 AND YL4) were inserted into the Cla I site of the derivative plasmid, resulting in the construction of pMCU-Bsr retaining only one Sal I, Cla I and Not I site (FIG. 10). pMCU-Bsr was used for the replacement of the alphoid YAC right arms by homologous recombination after the Sal I and Not I digestion.

Oligonucleotides used in this example were described as follows:

YL3:
  5'-CGTCGACCATCGATACCAATGCATTGGCGG CCGC-3'

YL4: 5'-CGGCGGCCGCCAATGCATTGGTATCGATG GTCGA-3'

EXAMPLE 3

RAD52 Plasmid Mediated Transient Homologous Recombination in rad52⁻ Host YAC Strains and Homologous Recombination Procedure For the centromere functional assay in vivo, the terminals of the linear DNA fragment should be stabilized to avoid integration, degradation from the ends and end replication problems. Therefore we replaced the left and right arms of these two YAC clones with human telomere sequences. YAC can be modified very easily using yeast homologous recombination systems (Pachnis et al 1990, Proc. Natl. Acad. Sci., 87, 5109–5113, Pavan, 1990, Proc. Natl. Acad. Sci., 87, 1300–1304), but in this case, a dilemma is presented because we used rad52⁻ host to stabilize the repetitive DNA in the YAC. To overcome this problem, we developed a retrofitting method that is transiently inducible in the rad52 host.

Figure 11:
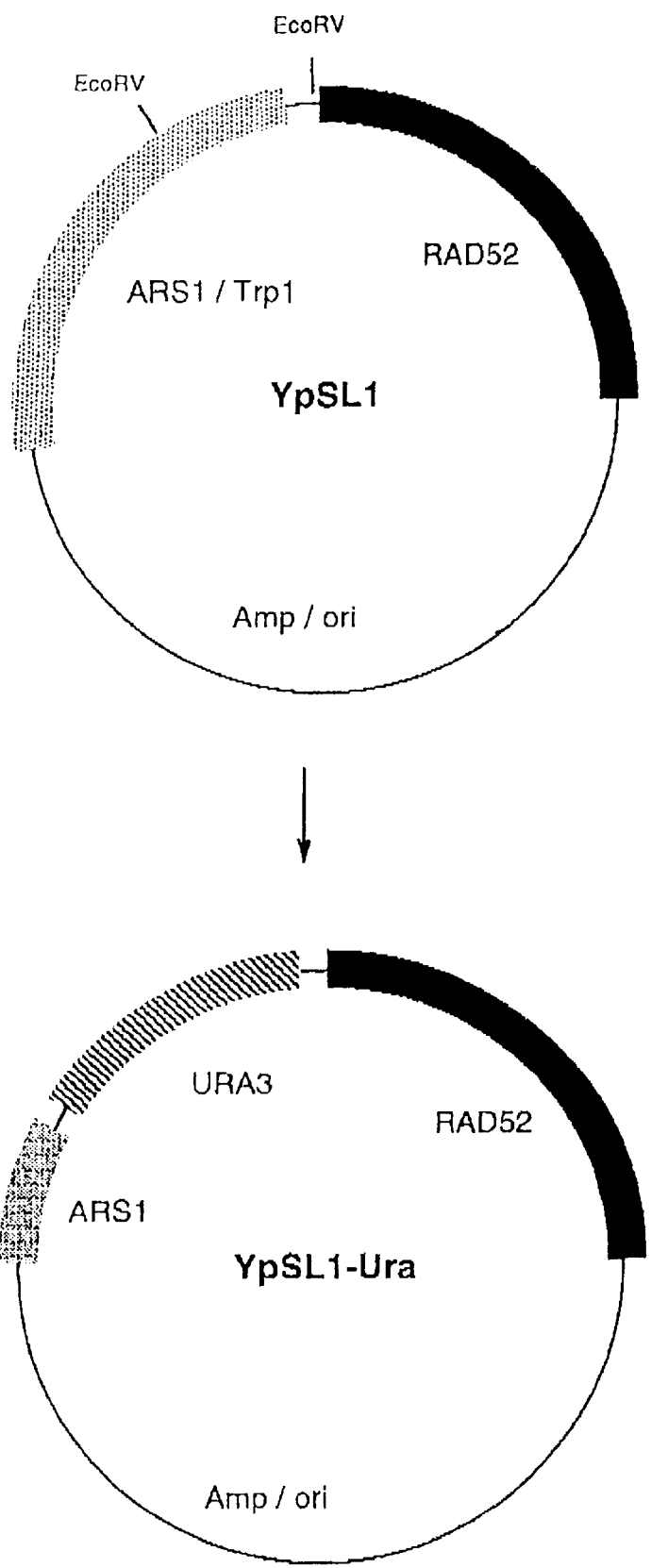
FIG. 11 shows YpSL1 and the construction of YpSL1Ura using YpSL1.
Figure 12:
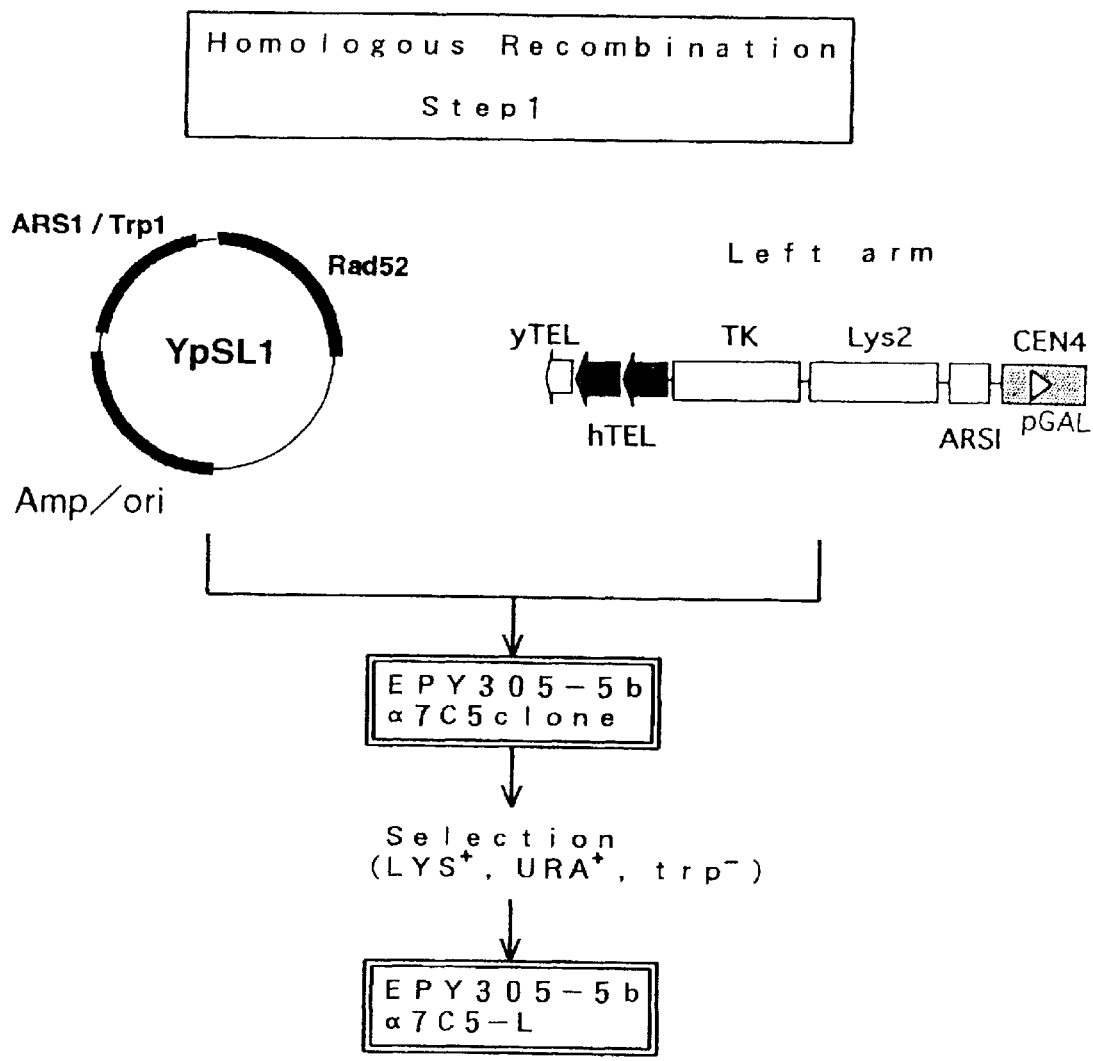
FIG. 12 shows a schematic of the procedure used for constructing the α7C5 left arm.
Figure 13:
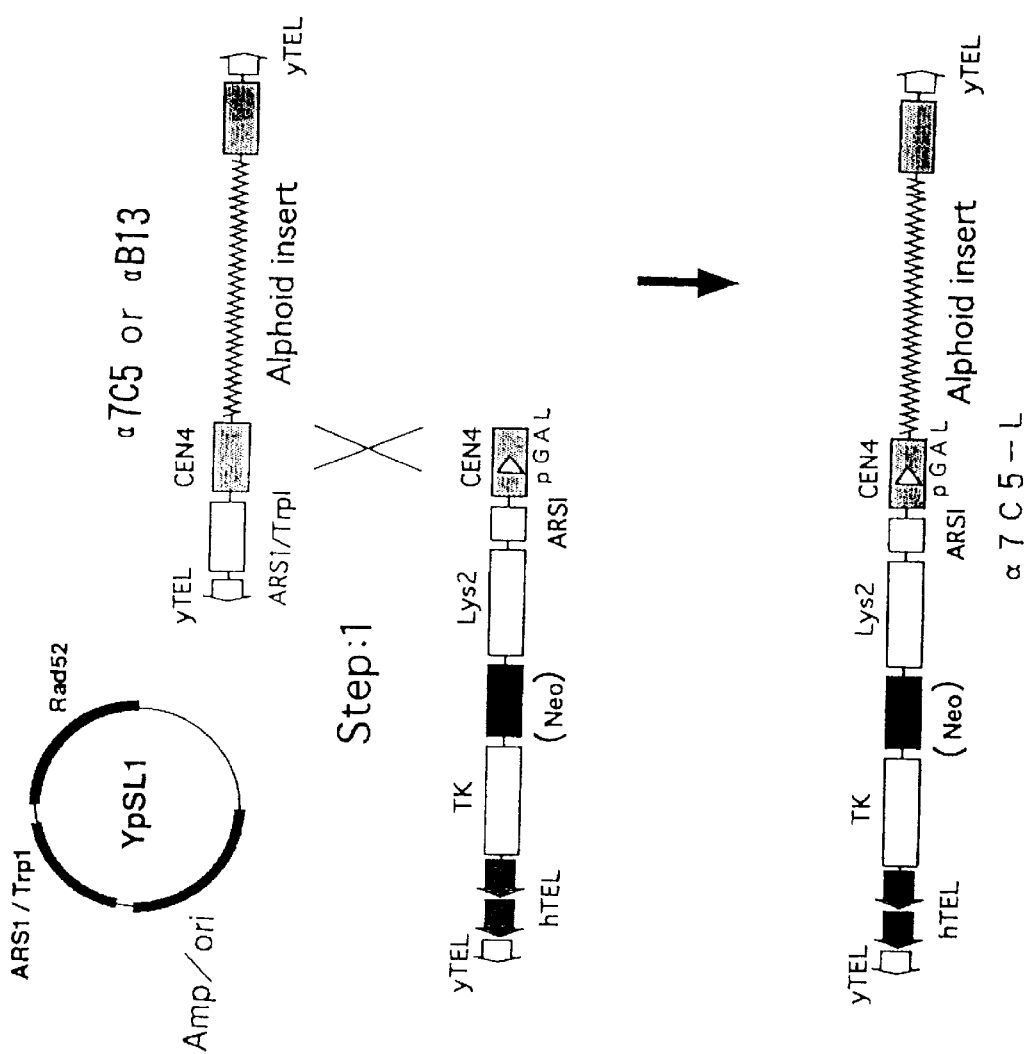
FIG. 13 shows a schematic diagram of the homologous recombination of the YAC left arm (step1).
Figure 14:
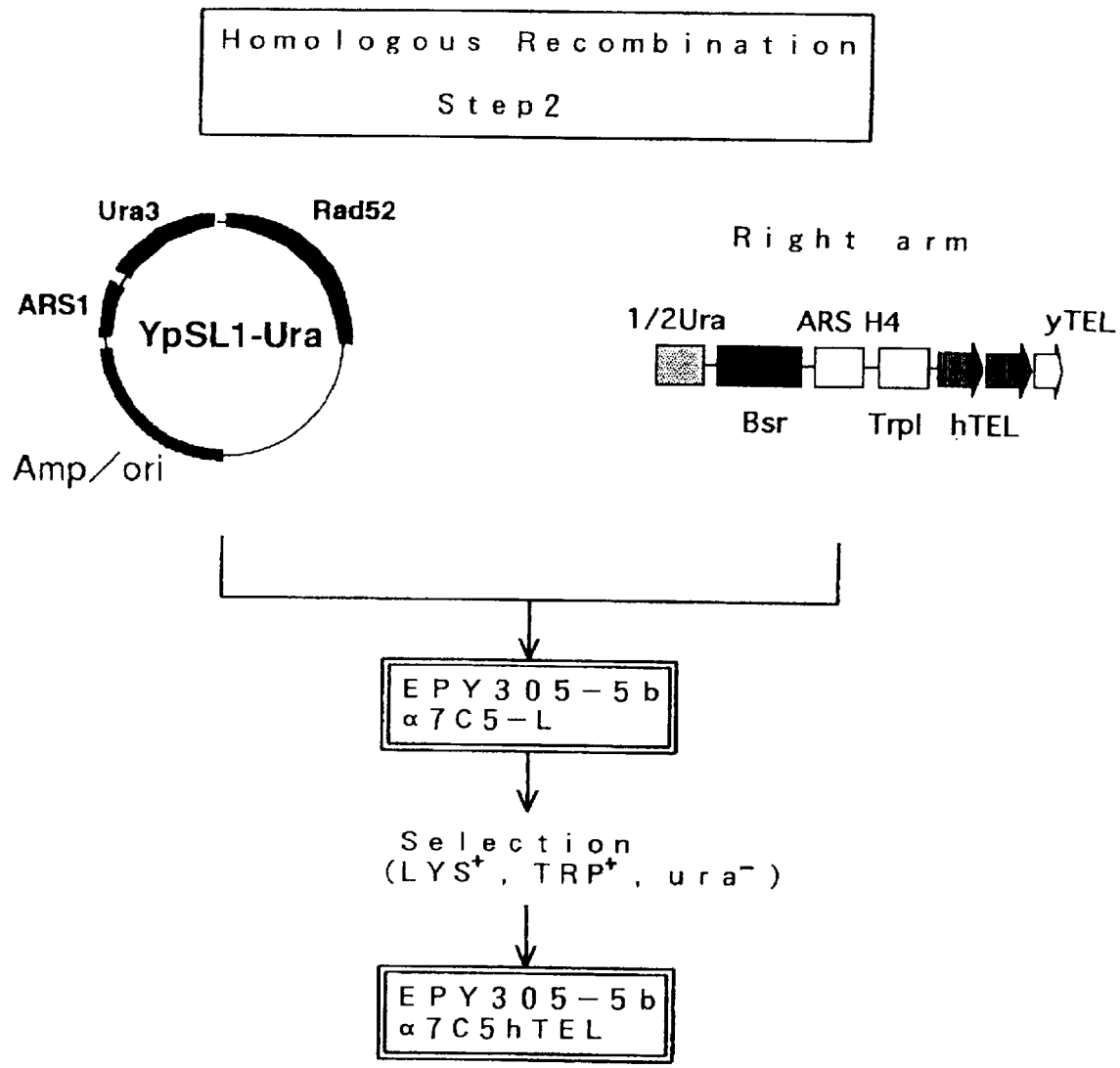
FIG. 14 shows a schematic of the procedure used for constructing α7C5hTEL
Figure 15:
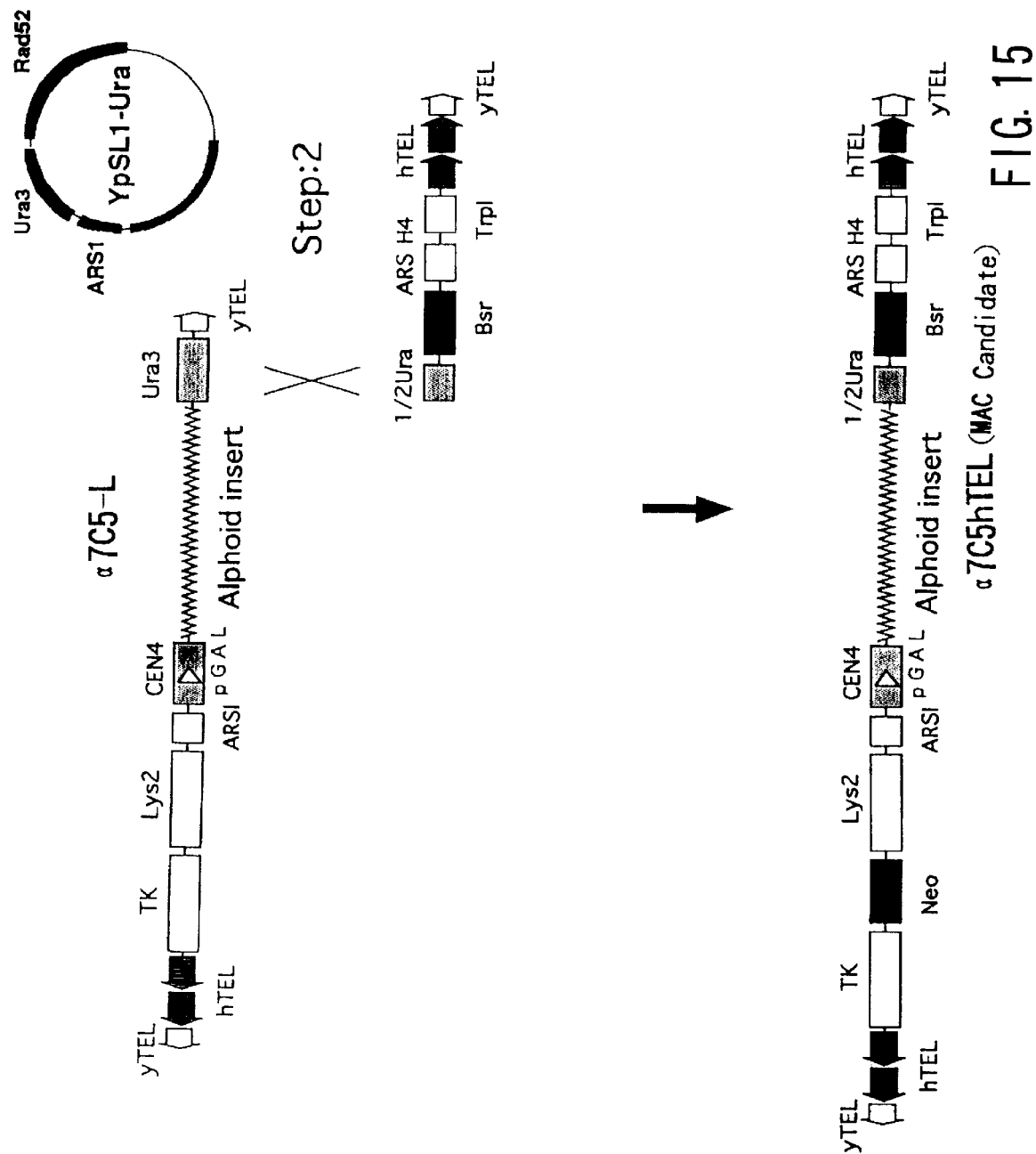
FIG. 15 shows a schematic diagram of the homologous recombination of the YAC right arm (step2), resulting in the construction of α7C5hTEL.
Figure 16:
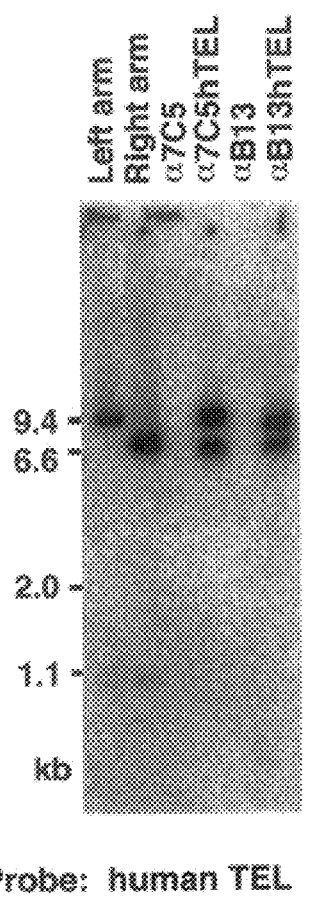
FIG. 16 shows recombined alphoid YACs digested with BamHI and hybridized with a human telomere sequence.
Figure 17:
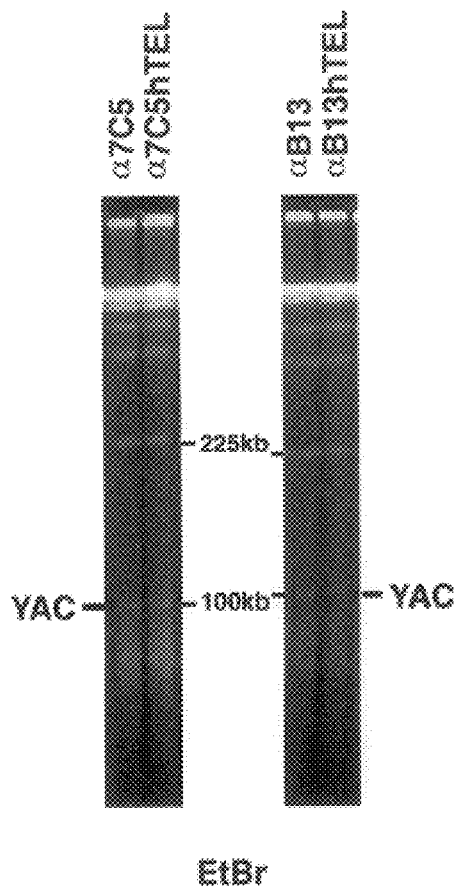
FIG. 17 shows the modified YACs after the recombination processes and analyzed using PFGE.

The alphoid YAC arms were replaced with the modified YAC vectors by homologous recombination mediated by transient expression of RAD52 gene in the rad 52⁻ host. In the first step, α7C5 or αB13 yeast cells were cotransfected with the linearized left arm replacement vector (MegaΔ or MegaSVNeo respectively) and a RAD52 expressing plasmid containing TRP1 gene (YpSL1) (FIGS. 11 and 12). A yeast colony showing +LYS, +URA and trp phenotype indicates that the left arm replacement was successfully carried out (FIG. 13). The RAD52 expressing plasmid, YpSL1, contains the yeast ARS fragment but no yeast CEN sequence. Therefore, the plasmid rapidly disappeared from the transfected cells in the absence of TRP selection. 14 to 30% of colonies showed trp phenotype among the colonies showing +LYS, +URA phenotype. The insert size and the replaced YAC arms of the clones were certified by PFGE and Southern analysis (FIG. 17). The clones which showed intact insert size were used for the second retrofitting with the linearized right arm replacement YAC vector (MCUBsr) and a RAD52 expressing plasmid containing URA3 gene (YpSL1URA)(FIGS. 11 and 14). In the second retrofitting, 23 to 42% of the colonies showed ura phenotype among the colonies showing +LYS, +TRP phenotype. Finally, we obtained desired YAC clones (MAC candidates, α7C5hTEL and αB13hTEL ) whose arms were replaced with new left and right YAC arms containing the human telomeres and the selection maker without the rearrangement of the insert alphoid DNAs (FIGS. 15, 16 and 17). This telomere modified YAC DNA was purified from the yeast cells using PFGE separation, agarase treatment and dialysis.

The detailed experimental procedure for this two steps homologous recombination process (FIGS. 12 and 14) is described below.

Two yeast rad52⁻ strains containing YACs, which have human chromosome 21 alphoid DNA insert called α7C5 (100 kb) and αB13 (110 kb) were used for RAD52 plasmid mediated transient homologous recombination. Each yeast strain was inoculated into 10 ml of a liquid selection medium, SD (1st; −ura −trp, 2nd; −lys −ura) and grown overnight to 1–2×10⁷ cells/ml (OD600=0.5-\f2 1.0). The cell culture was diluted to 2×10⁶ cell/ml with fresh medium and regrown to 1×10⁷ cell/ml. Then, the cells were harvested and washed with sterile water, re-suspended with 1.0 ml water and transferred into 1.5 ml microfuge tubes. The cells were washed with 1.0 ml of LiAc/TE and re-suspended at 2×10⁸–2×10⁹ cells/ml with LiAc/TE (50–500 μl).

50 μl of the yeast suspension was mixed with 500 ng of linearized YAC arm replacement vector DNA (1st step: MegaΔ for α7C5 or MegaSV-Neo for αB13, 2nd step:MCU-Bsr), 500 ng of an ARS plasmid containing RAD52 gene (1st:YpSL1 and 2nd:YpSL1-Ura) and 50 μg of single stranded salmon sperm carrier DNA, and then mixed with 300 μl of 40% PEG 4000 solution. The yeast and DNA mixture was incubated at 30° C. for 30 min with agitation and heat shocked at 42° C. for 15 min. The yeast cells were collected by spinning down for 5 sec. at 7000 rpm, re-suspended with 1 ml YPD and incubated at 30° C. with agitation for 2 hr. The yeast cells were collected and washed with the selection medium SD (1st: −lys −ura, 2nd: −trp −lys) and placed on the appropriate selection SORB plate. After 4–5 days of incubation at 25° C., colonies were replicated (with or without Trp) on the SORB plate (1st: +/−trp, 2nd: +/−ura) and incubated at 25° C. After 3–4 days of incubation, colonies showing appropriate phenotypes (1st: +LYS +URA −trp, 2nd: +TRP +LYS −ura) were collected and were analyzed for the insert size and the existence of human telomere by PFGE and Southern hybridization. In the first homologous recombination step, YAC55 pkc left arm was replaced with linearized MegaΔ or Mega SV-Neo. The frequency of colonies with a −trp/+LYS +URA phenotype for the 1st recombination was 14–30%. Yeast strains containing a correctly modified left arm YAC were used for the 2nd recombination of the right arm with linealized MCU-Bsr replacement vector. The frequency of colonies with a −ura/+TRP +LYS phenotype for the 2nd recombination was 23–42%. Yeast strains having both arms correctly modified were maintained on −lys −trp plates and used as the materials for YAC DNA purification and YAC DNA transfection into human cells.

The recombinant YAC containing the α7C5insert was designated as α7C5 h TEL. The recombinant YAC containing αB13 insert was designated as αB13 h TEL. *Saccharomyces cerevisiae* containing α7C5 h TEL (*Saccaromyces cerevisiae* EPY305-5b α7C5 h TEL) was deposited with the Agency of Industrial Science and Technology, National Institute of Bioscience and Human Technology (NIBH) on Aug. 14, 1996, and its deposit number is FERM BP-5625.

The LiAc/TE and 40% PEG solution used in this Example were prepared as follows:

LiAc/TE:
0.1M Li-Acetate pH7.5/10 mM Tris-HCl pH7.5/1 mM EDTA, freshly made from 10×Li/Ac (1M LiAc pH7.5 adjusted with acetic acid), TE.

40%PEG solution;
40%PEG 4000/0.1 M Li-Acetate pH7.5/10 mM Tris-HCl pH7.5/1 mM EDTA freshly made from 50% PEG4000, 10×LiAc, TE

EXAMPLE 4

Purification of Intact YAC DNA

Ten agarose plugs prepared from each yeast strain containing a retrofitted YAC (α7C5 h TEL, αB13 h TEL) were equilibrated with 1×TAE (40 mM Tris/40 mM Acetic Acid/1 mMEDTA), loaded on 1.2%LMP agarose (Seaplaque, FMC) in 1×TAE and PFGE was performed under the conditions of 200V, 4° C. and pulse time 15 sec. for 18–24 hours. A gel slice containing only YAC DNA from the preparative lanes was excised according to the size estimation of the EtBr staining of control lanes on either side. The gel slice containing YAC DNA was positioned vertically in the middle of the gel tray and 3% LMP agarose was cast around it. About 0.1 cm³ of the gel cube was removed from the bottom area in contact with the gel slice containing YAC DNA. In order to trap the DNA, a small piece of dialysis membrane was inserted at a position which is 0.5 cm from the gel slice and then gaps were filled with 1.5% LMP agarose. After conventional gel electrophoresis for 2 hr at 8 V/cm, a small piece of the 1.5% agarose area was recovered from immediately in front of the dialysis membrane in which the YAC DNA was concentrated, equilibrated with 1×TAE supplemented 100 mM NaCl and all the fluid was removed. Agarose from the gel was then melted at 68° C. for 10 min., incubated and digested with 50 U agarase (Sigma) per 1 ml of gel slice at 42° for 4 hr. The resulting YAC DNA solution was dialyzed (concentrated) using Ultra Free C3 (Millipore) or Microcon 100 (Amicon) against a buffer containing 100 mM NaCl, 10 mM Tris pH 7.5, and 1 mM EDTA and the concentration and the integrity of the DNA was checked by conventional gel and PFGE. Between 50 to 100 ng of purified DNA was obtained from this scale of experiments. Then the purified DNA was used as a material for YAC transfection into human culture cells by lipofection and microinjection.

EXAMPLE 5

YAC Transfection into Human Cells by Lipofection and by Microinjection

Our modified YAC constructs have total 1.1 kb human telomere sequences flanked by 0.3 kb yeast telomere sequences on both chromosome ends. However, to minimize the possibility that introduced YAC DNA will integrate into host chromosome by low telomerase activity of the host cells, we chose human HT1080 cells, which are reported as having high Telomere Associated Chromosome Fragmentation (TACF) activity (Barnett et al., 1993, Nucleic Acids Research, 21, 27–36), as the host. The purified YAC DNAs were introduced into human HT1080 cultured cells using two different methods: lipofection and microinjection into nuclei.

YAC Transfection by Lipofection

YAC transfections into HT1080 cells using lipofectamine (Gibco BRL) were basically carried out according to the manufacturer's instruction. Purified YAC DNA solution (30–100 ng DNA in 300 μl solution) was combined in a polystyrene tube with a premixed lipofectamine (10 μl) and serum free medium (100 μl of Opti-MEM, Gibco BRL) 30–40 min before the lipofection, mixed gently and stored for 30 min at RT to allow the DNA-liposome complex to form. HT1080 cells (9×105 cells) seeded in a 25 cm² flask were incubated overnight until 70–80% confluent and washed twice with 2 ml of Opti-MEM, and then all the medium was completely removed. The DNA-liposome complex solution was mixed gently with 1.6 ml of Opti-MEM (2 ml of total vol) and overlaid onto the rinsed cells. After 16 hr incubation at 37° C. in 5% CO2, the DNA-liposome complex solution was replaced with DME supplemented with 10% FCS, and the cells were allowed to incubate for 24 hr. Then, the cells were transferred into two 10 cm dishes, and selection with 4 mg/ml Blasticidine S(BS, Kaken Seiyaku) was started. Between 50 to 580 BS resistant colonies were obtained per μg of YAC DNA (α7C5 h TEL and αB13 h TEL, 110–120 Kb) transfections using lipofectamine and 410 to 470 BS resistant colonies were obtained per μg of linealized MCU-Bsr (11.2 kb) right arm vector (11.2 Kb) transfections.

YAC Transfection by Microinjection

YAC microinjection was carried out using a Zeiss Axiovert 135M equipped with an Eppendorf 5242 microinjector, a 5170 micromanipulator and a stage incubator and controller settled at 37° C. (Zeiss). HT1080 cells were grown on poly-D-lysine coated etched grid coverslips (Bellco Biotechnology) fixed in a 35 mm circular petri dish for 2 days. Immediately before injection, 3 ml of liquid paraffin oil (Boots Company) was added over the medium. After centrifugation at 12000 rpm for 5 min, 1.5 μl supernatant of purified YAC DNA solution was inserted into a microinjection needle (Eppendorf Femtotip) using an Eppendorf microloader tip, and microinjection was performed under the conditions of P1; 5000 hPa, P2; 30–60 hPa, P2; 30–60 hPa, P3; 15–30 hPa. After the microinjection, the liquid paraffin oil and the medium were removed from the dish, fresh medium was added, and the cells were incubated at 37° C. for 36 hr in 5% $CO_2$. Blasticidine S selection (4 mg/ml) was started at this point. In several experiments, the injected cells continued to grow on the etched cover slips, and derived BS resistant colonies were counted per injected cells on the grid and collected. In the rest of the experiments, the injected cells were transferred into a 10 cm dish and the BS selection was started. One BS resistant colony was obtained per every 100 to 300 YAC DNA injected cells.

EXAMPLE 6

The Fate of Alphoid YACs in HT1080 Cells

Figure 18A:
FIG. 18(a) shows a merged image of a FISH analysis of cell lines transformed with recombinant YAC. Metaphase chromosomes from cell line 7C5HT1 were hybridized with an α21-I probe (green signals) and a YAC arm probe (red signals). The chromosome was counter-stained with DAPI.
Figure 18B:
FIG. 18(b) shows a merged image of a FISH analysis of cell lines transformed with recombinant YAC. Metaphase chromosomes from cell line B13HT1 were hybridized with an α21-I probe (green signals) and a YAC arm probe (red signals). The chromosome was counter-stained with DAPI.
Figure 18C:
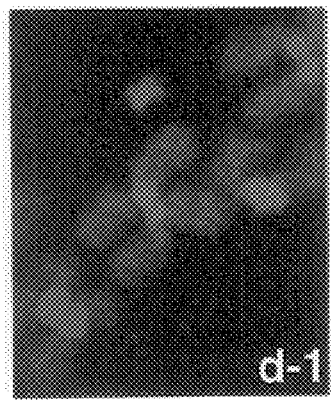
FIG. 18(c) shows a FISH analysis of cell lines transformed with recombinant YAC. Metaphase chromosomes from cell line H7C5HTm1 were hybridized with an α21-I probe (green signals) and a YAC arm probe (red signals). The chromosome was counter-stained with DAPI.

If these MAC candidates retain all the cis elements required for mammalian chromosome stability, e.g., telomeres, a functional centromere/kinetochore structure and a replication origin etc, YAC DNA introduced into the human cells may possibly be maintained without integrating into host chromosomes even after BS selections. To examine this possibility, we analyzed the distributions of the YAC DNA in 24, 20 and 5 cell lines of BS resistant colonies obtained from α7C5hTEL, αB13hTEL and the linearized MCUBsr vector introduced cells, respectively, by fluorescent in situ hybridization (FISH) (FIG. 18). Although the number of cells containing a mini-chromosome which is detectable as an extra chromosomal overlapping signals of the α21-I probe and the YAC vector probe varied from cell line to cell line, cells containing such a mini-chromosome were observed in most of the cell lines (11/13 cell lines or 10/11 cell lines) derived from α7C5hTEL YAC transfection (7C5HT cell lines), regardless of the introducing methods, i.e., lipofection or microinjection. The sizes of the mini-chromosomes detected by FISH varied in each clones and seemed to increase to the megabase order from the initial YAC constructs (~110 kb) through the establishment as a BS resistant cell line. 30% of the total analyzed metaphase cells from these cell lines have mini-chromosome signals (FIG. 19). Also, integration signals to the centromere and telomere regions of host chromosomes were observed in about 40% of the cells. However, the presence of a mini-chromosome and an integration event in the same cell was very rare (only 2.3% cells of two clones out of a total of 610 analyzed cells from 24 clones), and integration of the YAC into the host chromosome arms was also very rare (only 1.8% cells).

In contrast to these results, we could not obtain any signal indicating a mini-chromosome from a total of 400 and 100 metaphase cells derived from αB13hTEL YAC and the linearized MCUBsr vector introduction, respectively (FIG. 19). The results obtained from the cell lines derived from αB13hTEL YAC introduction (B13 HT cell lines) showed that the majority of the YAC integration occurred at the telomere region in 75% of cells (FIG. 19), centromere integration weas 14%, and integration into the host chromosome arms was also very rare (only 1.3% cells). However, although the results of the cell lines derived from the linearized MCUBsr vector introduction (MCUHT clones) showed that the telomere integration of the vector was 56%, no integration into the centromere region and 10 times higher score of the host arm integration (19%) were observed.

Interestingly, although the integration sites of the α7C5hTEL YAC into the centromere and telomere regions varied into several different chromosomes, cell by cell, in the same cell line, most of the integration of αB13hTEL YAC or the linearized MCUBsr vector in the same cell line were derived from a single site. These results indicate that the integration occurred as multiple events and independently through the establishment of 7C5HT cell lines. However, the integration occurred only once through the establishment of many B13HT or MCUHT cell lines.

All these results clearly indicate that α7C5hTEL YAC retains the elements required for de novo formation of a human mini-chromosome very efficiently, but, αB13hTEL does not.

EXAMPLE 7

Stability of Artificial Mini-Chromosome Without Selection

Previous reports indicated that extra-chromosomal elements without centromere function rapidly disappeared when the drug for the selection was excluded from the medium (Huxley). The stability of the mini-chromosome in three 7C5HT cell lines obtained by lipofection (7C5HT1, 2 and 3) and two 7C5HT cell lines obtained by microinjection (7C5HTm1 and 7C5HTm3) were analyzed both by FISH and colony formation efficiency on plate (plating efficiency: number of colonies on +BS selection against that on nonselective media) after the passage of 20, 40, 60 days on nonselective media (FIG. 20). Plating efficiency data from these 5 cell lines indicated that in all 5 cell lines more than 50% of the population maintained BS resistancy even after the passage of 60 days on nonselective media, and 97% of 7C5HT1 and 7C5HT3 cells maintained BS resistancy after the off selection. Corresponding to these data, the data from FISH analysis also indicated that the mini-chromosomes in 7C5HT1 and 7C5HT3 cell lines were very stable even after the passage of 60 days on nonselective media, and the mini-chromosomes in 7C5HT2, 7C5HTm1 and 7C5HTm3 cell lines were gradually lost through the passage of nonselective media. Interestingly, the sizes of mini-chromosomes in 7C5HT1 and 7C5HT3 cell lines were bigger than those in 7C5HT2, 7C5HTm1 and 7C5HTm3 cell lines. All the cell lines containing mini-chromosomes also have some integration events when each cell line was established after about 3040 days from the YAC DNA introduction. Therefore, the cells of 7C5HT1 were recloned (7C5HT11, 2, 4 to 9 and 19), and the stability of the mini-chromosomes in each cell lines were analyzed by FISH and the plating efficiency (FIG. 21). Ten colonies were isolated from 7C5HT1 cells, but one of them was lost during the establishment. Seven out of 9 established cell lines showed only mini-chromosome signals without any integration signal into the host chromosome, and the mini-chromosomes in 7C5HT11 cells were very stable (100%) with 1 or 2 copies through the passage on nonselective media from the both FISH and plating efficiency data. 7C5HT19 cells showed an integration signal at the centromere of a host chromosome and 7C5HT119 cells showed a telomere integration signal. BS resistances and the integration sites of B13HT cell lines and MCUHT cell lines were very stable and not changed after the passage through the off selection for 60 days (data not shown).

These data from plating efficiency and FISH analyses of 7C5HT cell lines clearly indicate that the mini-chromosomes derived from α7C5hTEL YAC were segregated stably through the cell divisions even in the condition without BS selection.

EXAMPLE 8

Functional Centromere/Kinetochore Structure on the Mini-Chromosome

Figure 22A:
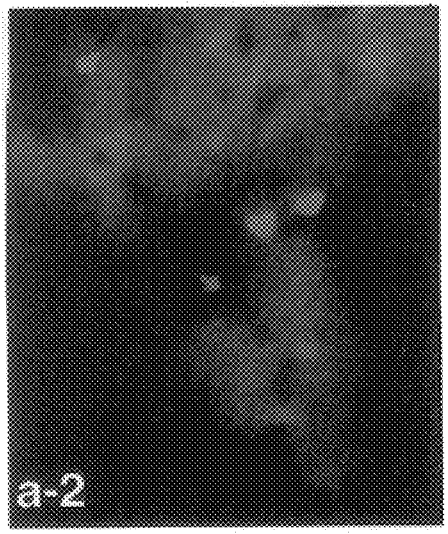
FIG. 22(a) shows a merged image of the detection of centromere antigens on mini-chromosomes and chromosomes. Metaphase chromosomes from cell lines 7C5HT2 were analyzed simultaneously by FISH with an α21-I probe (green signals in panel) and a YAC arm probe (red signals).
Figure 22B:
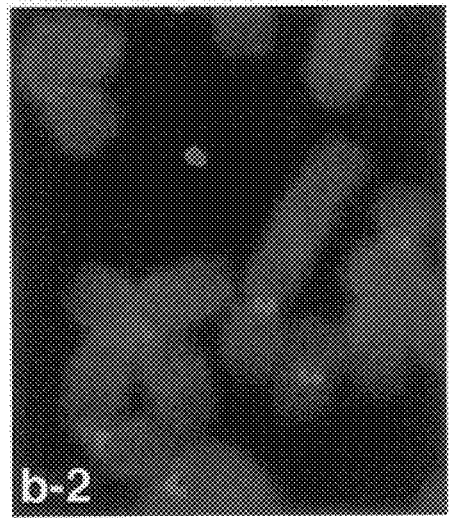
FIG. 22(b) shows a merged image of the detection of centromere antigens on mini-chromosomes and chromosomes. Metaphase chromosomes from cell lines 7C5HT2 were analyzed simultaneously by FISH with a YAC arm probe (red signals) and by indirect immunofluorescence with an anti-CENP-B antibody (green signals in panel).
Figure 22C:
FIG. 22(c) shows a merged image of the detection of centromere antigens on mini-chromosomes and chromosomes. Metaphase chromosomes from cell lines 7C5HT2 were analyzed simultaneously by FISH with a YAC arm probe (red signals) and by indirect immunofluorescence with an anti-CENPC antibody (green signals).
Figure 23A:
FIG. 23(a) shows a merged image of the detection of centromere antigens on mini-chromosomes and chromosomes. Metaphase chromosomes from cell lines 7C5HT12 were analyzed simultaneously by FISH with an α21-I probe (green signals in panel) and a YAC arm probe (red signals).
Figure 23B:
FIG. 23(b) shows a merged image of the detection of centromere antigens on mini-chromosomes and chromosomes. Metaphase chromosomes from cell lines 7C5HT12 were analyzed simultaneously by FISH with a YAC arm probe (red signals) and by indirect immunofluorescence with an anti-CENP-B antibody (green signals in panel).
Figure 23C:
FIG. 23(c) shows a merged image of the detection of centromere antigens on mini-chromosomes and chromosomes. Metaphase chromosomes from cell lines 7C5HT12 were analyzed simultaneously by FISH with a YAC arm probe (red signals) and by indirect immunofluorescence with an anti-CENP-C antibody (green signals).
Figure 24:
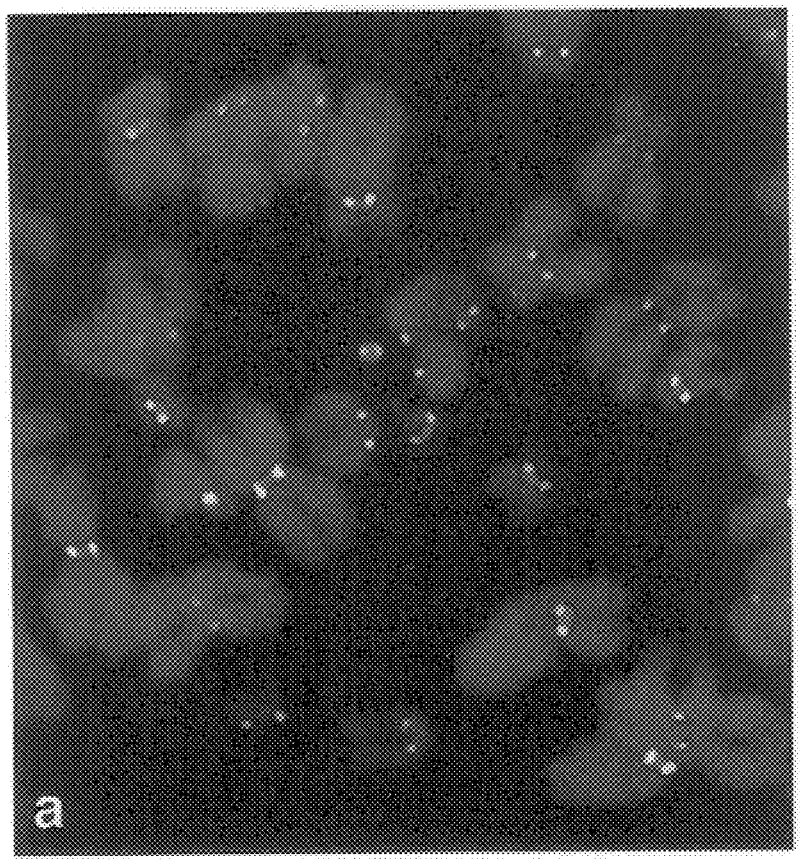
FIG. 24 shows metaphase chromosomes from the cell line 7C5HT1 detected by indirect immunofluorescence using both anti-CENP-B antibody (red signals) and anti-CENP-C antibody (green signals). The chromosomes were counter-stained with DAPI.

We have already shown in this application that an alphoid YAC containing CENP-B boxes in high frequency (α7C5hTEL YAC) could form mini-chromosomes at high frequency, although an alphoid YAC containing no CENP-B box (αB13hTEL YAC) could not. This result indicates that CENP-B must be an essentially important factor for de novo formation of functional centromere structure. CENP-C has reported to be localized at the inner layer of kinetochore structure and also reported to be localized only at the functional side of the centromeres in dicentric chromosomes (Saitoh et al. 1992, Cell, 70, 115–125, Sullivan, 1995, Hum. Mol. Gent., 4, 2189–2197). In order to clarify the molecular bases required for the functional centromere/kinetochore structure of human chromosomes, we analyzed distributions of these two centromere proteins on more than 20 each of mini-chromosomes in 7C5HT1, 11, 12, and 7C5HT2 cell lines derived from α7C5hTEL YAC introduction (FIGS. 22, 23 and 24) using simultaneous staining with indirect immuno-fluorescence and FISH. Clear CENP-B and CENP-C double dot signals were observed on all the mini-chromosomes which were detected simultaneously by the YAC vector probe, indicating that the mini-chromosomes contained essentially important protein factors as centromere/kinetochore components. We could not obtain any positive signals of CENP-B staining on the integration sites of αB13hTEL YAC in the B13HT1 cell line.

Figure 25A:
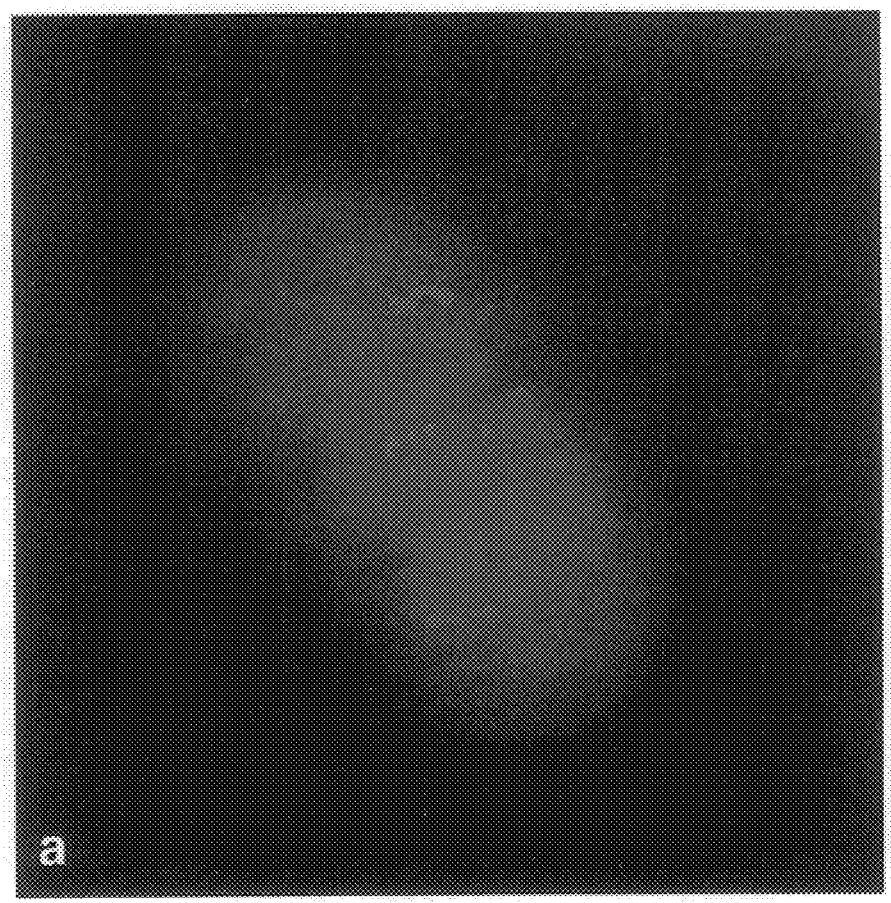
FIG. 25(a) shows metaphase cells of the 7C5HT12 cell line hybridized with an α21-I probe (green signals) and YAC arm probe (red signals).
Figure 25B:
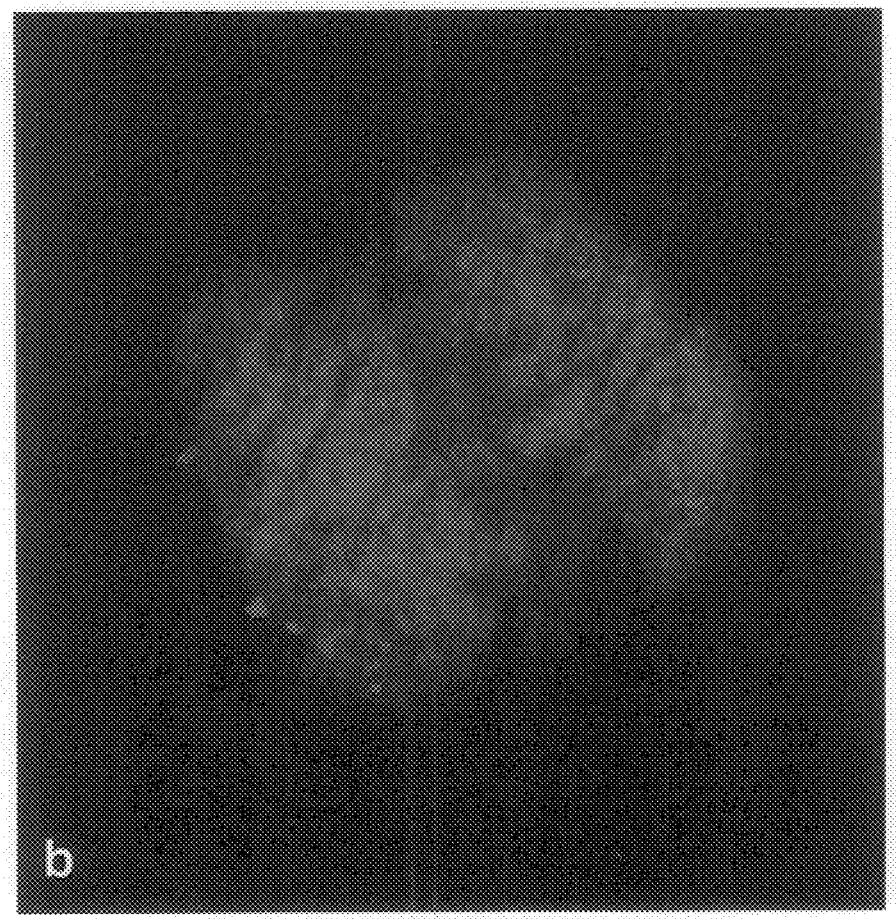
FIG. 25(b) shows anaphase cells of the 7C5HT12 cell line hybridized with an α21-I probe (green signals) and YAC arm probe (red signals).

Multiple previous reports which introduced the human alphoid DNA into mammalian cultured cells showed that anaphase lagging chromosomes were observed according to alphoid DNA integration into the host chromosomes and this phenomenon might be one of the functions of alphoid DNA. Therefore, we analyzed more than 50 of each of the metaphase and anaphase cells each from 7C5HT11, 12, 119 cell lines to determine whether the mini-chromosome is properly aligned at the metaphase plate or not, and to determine whether the sister chromatides of the mini-chromosome (or containing the integration) are segregated properly onto each spindle pole or not. All the mini-chromosomal signals from 7C5HT11 and 12 metaphase cells were aligned at the metaphase plate in parallel in the pole to pole direction, and all the sister chromatids signals of the mini-chromosomes from 7C5HT11 and 12 anaphase cells were segregated properly and located at the nearest edges of the chromatids to each pole (FIG. 25). No metaphase and anaphase lagging mini-chromosome (or lagging chromosome with the integrated signals) was observed from any 7C5HT11, 12 or even from 7C5HT119 cells. Our results indicate that the mini-chromosomes derived from α7C5hTEL YAC introduction retained proper centromere/kinetochore function and anaphase lagging is not a common phenomenon caused by alphoid DNA integration into the chromosome.

What is claimed is:

1. A recombinant DNA construct comprising:
    a mammalian centromere comprising spaced repeats of the sequence:
        5'-NTTCGNNNNANNCGGGN-3',
wherein N is selected from the group of A, T, C and G, and wherein the sequence is provided in a sufficient quantity to cause the recombinant DNA construct to form a mammalian artificial chromosome when introduced into a mammalian cell; and
    at least one DNA sequence that causes the DNA construct to also form an artificial chromosome when introduced into yeast or bacterial cells.

2. A recombinant DNA construct according to claim 1, further comprising a sequence encoding a selectable marker gene.

3. A recombinant DNA construct according to claim 1, further comprising a genome DNA sequence containing a structural region and its regulatory region.

4. A recombinant DNA construct according to claim 1, wherein the mammalian cell is a human or a mouse cell.

5. An isolated DNA sequence capable of providing a mammalian centromere property to a DNA construct when the DNA construct is introduced into a mammalian cell, said isolated DNA comprising spaced repeats of the sequence containing:
    5'-NTTCGNNNNANNCGGGN-3',
    wherein N is selected from the group of A, T, C and G.

6. An isolated DNA sequence according to claim 5, further comprising at least one DNA sequence that permits the DNA construct to form an artificial chromosome when introduced into yeast or bacterial cells, to autonomously replicate in yeast or bacterial cells, to be maintained extra chromosomally and to be transmitted to progeny cells thereof.

7. An isolated DNA sequence according to claim 5, further comprising a sequence encoding a selectable marker gene.

8. An isolated DNA sequence according to claim 5, which further comprises a genome DNA sequence containing a structural region and its regulatory region.

9. An isolated DNA sequence according to claim 5, wherein the mammalian cell is a mouse or a human cell.

10. A method of making an exogenous mammalian gene product, comprising:

introducing the recombinant DNA construct of claim 1 into a mammalian cell, wherein the recombinant DNA construct of claim 1 further comprises an exogenous DNA sequence encoding the mammalian gene product; and expressing the exogenous mammalian gene product.

11. A method of making an exogenous mammalian gene product, comprising:

introducing the isolated DNA sequence of claim 5 into a mammalian cell, wherein the isolated DNA sequence of claim 5 further comprises an exogenous DNA sequence encoding the mammalian gene product; and expressing the exogenous mammalian gene product.

\* \* \* \* \*

SEQUENCE LISTING (1) GENERAL INFORMATION:

(iii) NUMBER OF SEQUENCES:       7

(2) INFORMATION FOR SEQ ID NO: 1:

(i) SEQUENCE CHARACTERISTICS:
        (A) LENGTH:      17 base pairs
        (B) TYPE:        nucleic acid
        (C) STRANDEDNESS: double
        (D) TOPOLOGY:    linear (ii) MOLECULE TYPE:    peptide (vi) ORIGINAL SOURCE:
        (A) ORGANISM:  Homo sapiens (ix) FEATURE:
        (D) OTHER INFORMATION:   "N" stands for A, G, C or T.

(xi) SEQUENCE DESCRIPTION: SEQ ID NO: 1:

NTTCGTTGGA AACGGGA                                                  17

(2) INFORMATION FOR SEQ ID NO: 2:

(i) SEQUENCE CHARACTERISTICS:
        (A) LENGTH:      1868 base pairs
        (B) TYPE:        nucleic acid
        (C) STRANDEDNESS: double
        (D) TOPOLOGY:    linear (ii) MOLECULE TYPE:    DNA (genomic)

(vi) ORIGINAL SOURCE:
        (A) ORGANISM:  Homo sapiens (xi) SEQUENCE DESCRIPTION: SEQ ID NO: 2:

AATTCAAATA AAAGGTAGAC AGCAGCATTC TCAGAAATTT CTTTCTGATG TCTGCATTCA     60

ACTCATAGAG TTGAAGATTG CCTTTCATAG AGCAGGTTTG AAACACTCTT TCTGGAGTAT      120

CTGGATGTGG ACATTTGGAG CGCTTTGATG CCTACGGTGG AAAAGTAAAT ATCTTCCATA      180

AAAACGAGAC AGAAGGATTC TCAGAAACAA GTTTGTGATG TGTGTACTCA GCTAACAGAG      240

TGGAACCTTT CTTTTTACAG AGCAGCTTTG AAACTCTATT TTTGTGGATT CTGCAAATTG      300

ATATTTAGAT TGCTTTAACG ATATCGTTGG AAAAGGGAAT ATCGTCATAC AAAATCTAGA      360

CAGAAGCATT CTCACAAACT TCTTTGTGAT GTGTGTCCTC AACTAACAGA GTTGAACCTT      420

TCTTTTGATG CAGCAGTTTG GAAACACTCT TTTTGTAGAA ACTGTAAGTG GATATTTGGA      480

TAGCTCTAAC GATTTCGTTG GAAACGGGAA TATCATCATC TAAATCTAG ACAGAAGCAC       540

TATTAGAAAC TACTTGGTGA TATCTGCATT CAAGTCACAG AGTTGAACAT TCCCTTACTT      600

TGAGCACGTT TGAAACACTC TTTTGGAAGA ATCTGGAAGT GGACATTTGG AGCGCTTTGA      660

CTGCCTTTGT TGAAAAGGAA ACGTCTTCCA ATAAAAGCCA GACAGAAGCA TTCTCAGAAA      720

CTTGTTCGTG ATGTGTGTAC TCAACTAAAA GAGTTGAACC TTTCTATTGA TAGAGCAGTT      780

TTGAAACACT CTTTTTGTGG ATTCTGCAAG TGGATATTTG GATTGCTTTG AGGATTTCGT      840

TGGAAGCGGG AATTCGTATA AAAACTAGAC AGCAGCATTC CCAGAAATTT CTTTCGGATA      900

TTTCCATTCA ACTCATAGAG ATGAACATGG CCTTTCATAG AGCAGGTTTG AAACACTCTT      960

TTTGTAGTTT GTGGAAGTGG ACATTTCGAT CGCCTTGACG CCTACGGTGA AAAAGGAAAT     1020

ATCTTCCCAT AAAAATAGAC AGAAGCATTC TCAGAAACTT GTTGGTGATA TGTGTCTCAA     1080

CTAACAGAGT TGAACTTTGC CATTGATAGA GAGCAGTTTT GAAACACTCT TTTTGTGGAA     1140

TCTGCAAGTG GATATTTGGA TAGCTTGGAG GATTTCGTTG GAAGCGGGAA TTCAAATAAA     1200

AGGTAGACAG CAGCATTCTC AGAAATTTCT TTCTGATGAC TGCATTCAAC TCATAGAGTT     1260

GAACATTCCC TTTCATAGAG CAGGTTTGAA ACACTCTTTC TGGAGTATCT GGATGTGGAC     1320

ATTTGGAGCG CTTTGATGCC TATGGTGAAA AGTAAATAT CTTCCCATAA AAACGAGACA      1380

GAAGGATTCT GAGAAACAAG TTTGTGATGT GTGTACTCAG CTAACAGAGT GGAACCTCTC     1440

TTTTGATGCA GCAGTTTGGA AACACTCTTT TTGTAGAAAC TGTAAGTGGA TATTTGGATA     1500

GCTCTAATGA TTTCGTTGGA AACGGGAATA TCATCATCTA AAATCTAGAC AGAAGCCCTC     1560

TCAGAAACTA CTTTGTGATA TCTGCATTCA AGTCACAGAG TTGAACATTC GCTTTCTTAG     1620

AGCACGTTGG AAACACTCTT TTTGTAGTGT CTGGAAGTGG ACATTGGAG CGCTTTGATG      1680

CCTTTGGTGA AAAAGGGAAT GTCTTCCCAT AAAAACTAGA CAGAAGCATT CTCAGAAACT     1740

TGTTTTTGAT GTGTGTACCC AGCCAAAGGA GTTGAACATT TCTATTGATA GAGCAGTTTT     1800

GAAACACTCT TTTTGTGGAA AATGCAGGTG GATATTTGGA TAGCTTGGAG GATTTCGTTG     1860

GAAGCGGG                                                              1868

(2) INFORMATION FOR SEQ ID NO: 3:

(i) SEQUENCE CHARACTERISTICS:
        (A) LENGTH:     338 base pairs
        (B) TYPE:       nucleic acid
        (C) STRANDEDNESS: double
        (D) TOPOLOGY:   linear (ii) MOLECULE TYPE:   DNA (genomic)

(iv) ORIGINAL SOURCE:
        (A) ORGANISM: Homo sapiens (xi) SEQUENCE DESCRIPTION: SEQ ID NO: 3:

-continued

| | |
|---|---|
| AATTCGTATA AACACTAGAC AGCAGCATTC CCAGAAATTT CTTTCGGATA TTTCCATTCA | 60 |
| ACTCATAGAG ATGAACATGG CCTTTCATAG AGCAGGTTTG AAACACTCTT TTTGTAGTTT | 120 |
| GTGGAAGTGG ACATTTCGAT CGCCTTGACG CTACGGTGAA AAAGGAAATA TCTTCCCATA | 180 |
| AAAAATAGAC AGAAGCATTC TCAGAAACTT GTTGGTATAT GTGTACTCAA CTAACAGAGT | 240 |
| TGAACTTTGC CATTGATAGA GAGCAGTTTT GAAACACTCT TTTCGTGGAA TCTGCAAGTG | 300 |
| GATATTTGGA TAGCTTGGAG GATTTCGTTG GAAGCGGG | 338 |

(2) INFORMATION FOR SEQ ID NO: 4:

(i) SEQUENCE CHARACTERISTICS:
  (A) LENGTH:  339 base pairs
  (B) TYPE:  nucleic acid
  (C) STRANDEDNESS: double
  (D) TOPOLOGY:  linear (ii) MOLECULE TYPE: DNA (genomic)

(iv) ORIGINAL SOURCE:
  (A) ORGANISM: Homo sapiens (xi) SEQUENCE DESCRIPTION: SEQ ID NO: 4:

| | |
|---|---|
| AATTCGTATA AACACTAGAC AGCAGCATTC CCAGAAATTT CTTTCGGATA TTTCCATTCA | 60 |
| ACTCATAGAG ATGAACATGG CCTTTCATAG AGCAGGTTTG AAACACTCTT TTTGTAGTTT | 120 |
| GTGGAAGTGG ACATTTCGAT CGCCTTGACG CCTACGGTGA AAAAGGAAAT ATCTTCCCAT | 180 |
| AAAAAATAGA CAGAAGCATT CTCAGAAACT TGTTGGTGAT ATGTGTCCTC AACTAACAGA | 240 |
| GTTGAACTTT GCCATTGATA GAGAGCAGTT TTGAAACACT CTTTTTGTGG AATCTGCAAG | 300 |
| TGATATTTGA ATAGTTTGGA GGATTTCGTT GGAAGCGGG | 339 |

(2) INFORMATION FOR SEQ ID NO: 5:

(i) SEQUENCE CHARACTERISTICS:
  (A) LENGTH:  339 base pairs
  (B) TYPE:  nucleic acid
  (C) STRANDEDNESS: double
  (D) TOPOLOGY:  linear (ii) MOLECULE TYPE: DNA (genomic)

(iv) ORIGINAL SOURCE:
  (A) ORGANISM: Homo sapiens (xi) SEQUENCE DESCRIPTION: SEQ ID NO: 5:

| | |
|---|---|
| AATTCGTATA AACACTAGAC AGCAGCATTC CCAGAAATTT CTTTCGGATA TTTCCATTCA | 60 |
| ACTCATAGAG ATGAACATGG CCTTTCATAG AGCAGGTTTG AAACACTCTT TTTGTAGTTT | 120 |
| GTGGAAGTGG ACATTTCGAT CGCCTTGACG GCTACGGTGA AAAAGGAAAT ATCTTCCCAT | 180 |
| AAAAAATAGA CAGAAGCATT CTCAGAAACT TGTTGGTGAT ATGTGTCCTC AACTAACAGA | 240 |
| GTTAAACTTT GCCATTGATA GAGAGCAGTT TTGAAACACT CTTTTTTTGG AATCTGCAAG | 300 |
| TGATATTTGA ATAGTTTGGA GGATTTCGTT GGAAGCGGG | 339 |

-continued (2) INFORMATION FOR SEQ ID NO: 6:

(i) SEQUENCE CHARACTERISTICS:
        (A) LENGTH:       340 base pairs
        (B) TYPE:         nucleic acid
        (C) STRANDEDNESS: double
        (D) TOPOLOGY:     linear (ii) MOLECULE TYPE:     DNA (genomic)

(iv) ORIGINAL SOURCE:
        (A) ORGANISM:  Homo sapiens (xi) SEQUENCE DESCRIPTION: SEQ ID NO:  6:

```
AATTCGTATA AAAACTAGAC AGCAGCATTC CCAGAAATTT CTTTCGGATA TTTCCATTCA      60

ACTCATAGAG ATGAACATGG CCTTTCATAG AGCAGGTTTG AAACCCTCTT TTTGTAGTTT     120

GTGGACAGTG GACATTTCGA TCGTCTTGAC GCCTACGGTG AAAAAGGAAA TATCTTCCCA     180

TAAAAAATAG ACAGAAGCAT TCTCAGAAAC TTGTTGGTGA TATGTGTCCT CAACTAACAG     240

AGTTGAACTT TGCCATTGAT AGAGAGCAGT TTTGAAACAC TCTTTTTGTG GAATCTGCAA     300

GTGATATTTG AATAGCTTGG AGGATTTCGT TGGAAGCGGG                           340
```

(2) INFORMATION FOR SEQ ID NO: 7:

(i) SEQUENCE CHARACTERISTICS:
        (A) LENGTH:       338 base pairs
        (B) TYPE:         nucleic acid
        (C) STRANDEDNESS: double
        (D) TOPOLOGY:     linear (ii) MOLECULE TYPE:     DNA (genomic)

(iv) ORIGINAL SOURCE:
        (A) ORGANISM:  Homo sapiens (xi) SEQUENCE DESCRIPTION: SEQ ID NO:  7:

```
AATTCGTATA AAAACTAGAC AGCAGCATTC CCAGAAATTT CTTTCGGATA TTTCCATTCA      60

ACTCATAGAG ATGAACATGG CCTTTCATAG AGCAGGTTTG AAACACTCTT TTTGTAGTTT     120

GTGGAAGTGG ACATTTCGAT CGCCTTGACG CCTACGGTGA AAAAGGAAAT ATCTTCCCAT     180

AAAAATAGAC AGAAGCATTC TCAGAAACTT GTTGGTGATA TGTGTCTCAA CTAACAGAGT     240

TGAACTTTGC CATTGATAGA GAGCAGTTTT GAAACACTCT TTTGTGGAA TCTGCAAGTG      300

GATATTTGGA TAGTTTGGAG GATTTCGTTG GAAGCGGG                             338
```